(12) United States Patent
Noguchi et al.

(10) Patent No.: US 7,875,126 B2
(45) Date of Patent: Jan. 25, 2011

(54) METHOD OF SUPPLYING GAS TO MEDICAL INSTRUMENTS FOR WATER LEAKAGE EXAMINATION

(75) Inventors: Toshiaki Noguchi, Tokyo (JP); Eiri Suzuki, Sagamihara (JP)

(73) Assignee: Olympus Medical Systems Corporation, Tokyo (JP)

( * ) Notice: Subject to any disclaimer, the term of this patent is extended or adjusted under 35 U.S.C. 154(b) by 1096 days.

(21) Appl. No.: 11/599,812

(22) Filed: Nov. 15, 2006

(65) Prior Publication Data
US 2007/0169799 A1 Jul. 26, 2007

(30) Foreign Application Priority Data
Nov. 15, 2005 (JP) ............................. 2005-330602

(51) Int. Cl.
*B08B 3/14* (2006.01)
(52) U.S. Cl. ................................ 134/42; 73/40; 73/49.2
(58) Field of Classification Search ................... 134/42; 73/40, 49.2
See application file for complete search history.

(56) References Cited

U.S. PATENT DOCUMENTS

| | | | | |
|---|---|---|---|---|
| 4,506,544 A * | 3/1985 | Shimizu | ..................... | 73/45.5 |
| 5,494,530 A * | 2/1996 | Graf | ............................ | 134/18 |
| 5,882,589 A * | 3/1999 | Mariotti | ....................... | 422/28 |
| 6,412,334 B1 * | 7/2002 | Kral et al. | ...................... | 73/40 |
| 6,585,943 B1 * | 7/2003 | Sanford et al. | .............. | 422/307 |
| 6,814,932 B2 * | 11/2004 | Hlebovy et al. | ............... | 422/28 |
| 2001/0032494 A1 * | 10/2001 | Greszler | ........................ | 73/40 |
| 2002/0001537 A1 * | 1/2002 | Hlebovy et al. | ............... | 422/28 |
| 2006/0252991 A1 * | 11/2006 | Kubach | ...................... | 600/118 |

FOREIGN PATENT DOCUMENTS

| | | |
|---|---|---|
| DE | 101 25 521 A1 | 11/2002 |
| JP | 05-220110 | 8/1993 |
| JP | 09-253029 | 9/1997 |
| JP | 2001-46477 | 2/2001 |
| JP | 2002-65607 | 3/2002 |
| JP | 2003-79572 | 3/2003 |

* cited by examiner

*Primary Examiner*—Michael Barr
*Assistant Examiner*—Jason Heckert
(74) *Attorney, Agent, or Firm*—Scully, Scott, Murphy & Presser, P.C.

(57) ABSTRACT

There is provide an apparatus for washing and disinfecting an endoscope having a duct for detecting a water leakage, the duct having an opening to which a fitting is attached. The apparatus comprises a nozzle unit having a nozzle to supply a gas into the duct via the fitting in a case where the nozzle is inserted into the fitting and a base member holding the nozzle member. The apparatus further comprises a gas supplying unit capable of supplying the gas to the nozzle, a shifting unit capable of shifting the base member toward the fitting of the endoscope, and a controlling unit controlling drive of the shifting unit to shift the base toward the fitting and to drive of the gas supplying unit to allow the nozzle to blow the gas from before the nozzle reaches the fitting.

3 Claims, 22 Drawing Sheets

METHOD OF SUPPLYING GAS TO MEDICAL INSTRUMENTS FOR WATER LEAKAGE EXAMINATION

CROSS REFERENCE TO RELATED APPLICATIONS

The patent application is related to and incorporates by reference to Japanese Patent Application No. 2005-330602 filed on Nov. 15, 2005.

BACKGROUND OF THE INVENTION

1. The Field of the Invention

The present invention relates to an apparatus for washing and disinfecting a medical instrument and a method of supplying a gas to a medical instrument for water leakage examination and, more particularly, to an apparatus for automatically washing and disinfecting a medical instrument, inserted to a body of a specimen, such as a used endoscope and a method of controlling such an apparatus.

2. Related Art

An endoscope, used for the purpose of inspecting and curing body cavities of an object, has not only an external surface of an inserting section to be inserted to the body cavity but also various ducts, forming the endoscope ducts, such as an air supply duct, a suction duct, a fore water supply duct, a therapeutic-tool insertion duct and the like, all of which suffer from contaminants. Therefore, not only the external surface but also interiors of the respective ducts of the used endoscope need to be washed and disinfected.

In general, when performing steps of washing and disinfecting the endoscope using a washing and disinfecting apparatus, initially, the used endoscope is accommodated in and set to a washing and disinfecting bath of an apparatus body. Then, for the purpose of washing and disinfecting an interior of the endoscope duct, various supply nozzles, for fluid such as liquid or gas to be supplied into the endoscope duct, and various duct fittings opened to an external surface of the endoscope are connected to each other via tubes or the like.

Further, with a view to perform water-leakage checking to find whether or not the endoscope has voids communicating with the outside, that is, whether or not a water leakage area is formed, a leaked water detecting fitting communicating with an inside of the endoscope and a leaked water detecting nozzle, for supplying gas, are connected to each other via a tube or the like.

Subsequently, after the washing and disinfecting bath is closed with a cover body, an operation start switch is turned on. Then, first, gas is supplied from the leaked water detecting nozzle to the interior of the endoscope in a given volume and, thereafter, a sensor of the washing and disinfecting apparatus measures a pressure or the like, thereby performing step of checking water leakage.

Thereafter, the water leakage checking result has no problem, washing step is initiated and, then, disinfecting step is started. During washing step, initially, the washing and disinfecting bath is supplied with washing liquid. Then, when washing liquid has reached a given water level, washing is initiated. Washing liquid is circulated to allow a water stream to clean the external surface of the endoscope.

When this takes place, washing liquid, drawn by a circulation pump, in the washing and disinfecting bath is introduced to the respective ducts of the endoscope via tubes and duct connection ports. This allows the respective ducts of the endoscope to be washed with a water pressure of the introduced washing liquid. Also, washing liquid, to be introduced to the respective ducts of the endoscope, is not limited to washing liquid drawn by the circulation pump.

Upon completion of washing step, the operation goes to disinfecting step and, before that, washing liquid is washed out of the external surface of the endoscope and the ducts at a given washed level using tap water filtered upon given filtration. As the operation shifts to disinfecting step, the washing and disinfecting bath is supplied with disinfecting liquid, adjusted in a given concentration, in place of previously used washing liquid supplied in the preceding washing step.

At this moment, further, disinfecting liquid, discharged from the respective duct nozzles and drawn by the circulation pump to be fed to the washing and disinfecting bath, is introduced to the respective ducts of the endoscope through the associated tubes and duct fittings due to a water pressure generated by the circulation pump. In addition, disinfecting liquid to be introduced to the ducts of the endoscope is not limited to disinfecting liquid drawn by the circulation pump.

After disinfecting liquid has been supplied to the external surface and the ducts of the endoscope, the endoscope is immersed in disinfecting liquid for a while. Upon completion of disinfecting step in a given pattern, disinfecting liquid is washed out of various parts by tap water. Thereafter, supplying air or alcohol to the external surface and ducts of the endoscope promotes the drying of the external surface and ducts of the endoscope, after which a series of steps is completed.

Thus, since not only the external surface of the endoscope but also the ducts of the endoscope is washed and disinfected, the washing and disinfecting apparatus, including the endoscope washing bath provided with various supply nozzles, is disclosed for instance in Patent Document 1 (Japanese Patent Application Publication No. 9-253029).

When washing and disinfecting the endoscope using the endoscope washing and disinfecting apparatus disclosed in Patent Document 1 (Japanese Patent Application Publication No. 9-253029), all of the duct fittings, incorporated in the endoscope, need to be connected to the respective supply nozzles associated with the respective ducts as mentioned above.

However, in a case where the endoscope internally has a large number of ducts, that is, in a case where a large number of duct fittings is employed, it takes increased man-hours for the tubes to be connected. In addition, the work for connecting the tubes is relied on manpower and the larger the number of tubes to be connected, the greater will be the time required for the work of confirming whether or not the tubes are correctly connected. As a result, an issue arises with an increase in time required for washing and disinfecting the endoscope.

Thus, it is conceivable to utilize a technique of automatically inserting the respective supply nozzles to the fittings of the respective ducts. However, with liquid adhered onto the neighborhood of a connecting area of a leaked water detecting nozzle, if the leaked water detecting nozzle, for gas to be fed, is connected to a leaked water detection fitting connected to an inside of the endoscope, even liquid droplets are caused to be captured into the leaked water detecting fitting. This results in a consequence in which liquid penetrates into the inside of the endoscope, causing increased probabilities to occur with the occurrence of troubles in the endoscope.

SUMMARY OF THE INVENTION

Thus, the present invention has been completed with the above view in mind and has an object to provide a medical instrument washing and disinfecting apparatus, in which, during a phase of achieving the connections between nozzles and fittings, a leaked water detecting fitting can prevent liquid from entering into an inside of the endoscope, and a method of controlling such an apparatus.

A further object of the present invention is to, in addition to the above object, automatically connect supply nozzles to various duct fittings of the endoscope.

To achieve the above object, as one aspect, the present invention provides an apparatus for washing and disinfecting an endoscope having a duct for detecting a water leakage, the duct having an opening to which a fitting is attached, the apparatus comprising: a nozzle unit having a nozzle to supply a gas into the duct via the fitting in a case where the nozzle is inserted into the fitting; a base member holding the nozzle member; a gas supplying unit capable of supplying the gas to the nozzle; a shifting unit capable of shifting the base member toward the fitting of the endoscope; and a controlling unit controlling drive of the shifting unit to shift the base toward the fitting and to drive of the gas supplying unit to allow the nozzle to blow the gas from before the nozzle reaches the fitting.

Further, another aspect of the present invention provides a method of supplying a gas through a nozzle to a fitting attached to an opening of a duct provided in an endoscope to sense a water leakage of the endoscope, comprising steps of: starting the supply of the gas through the nozzle under a condition in which the nozzle is apart from the opening; shifting the nozzle toward the opening after the start of the supply of the gas; and inserting the nozzle into the opening continuously followed by the shifting step.

According to the present invention, in washing and disinfecting process, the supply nozzles can be automatically connected to the respective duct fittings of the endoscope and, during connecting work, a leaked water detection fitting can prevent liquid from entering into the Inside of the medical instrument such as the endoscope.

DETAILED DESCRIPTION OF PREFERRED EMBODIMENTS

Now, medical instrument washing and disinfecting apparatuses of various embodiments according to the present invention are described below with reference to the accompanying drawings.

First Embodiment

Figure 1:
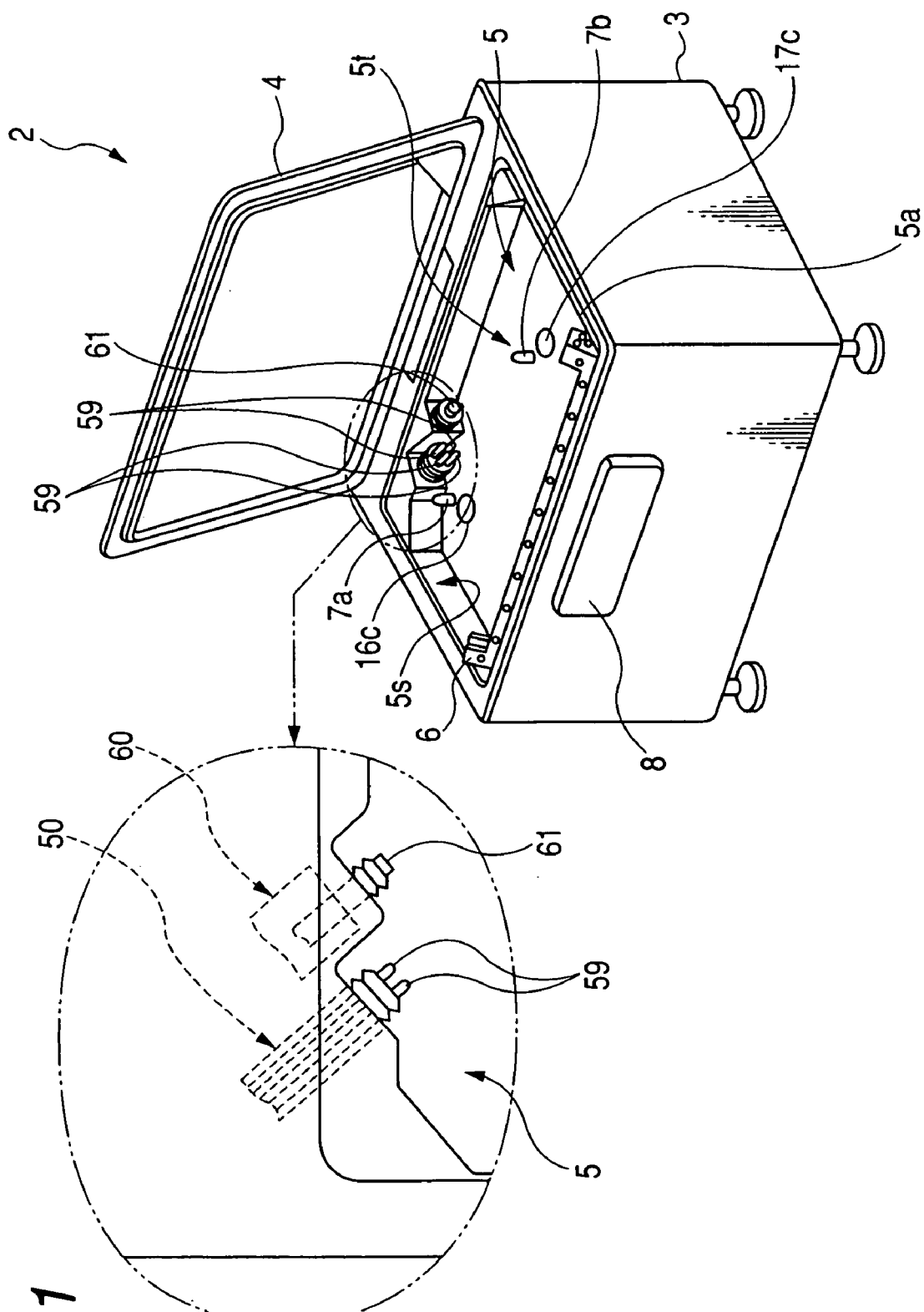
FIG. 1 is a perspective view showing an endoscope washing and disinfecting apparatus of a first embodiment according to the present invention with a top cover being opened.
Figure 2:
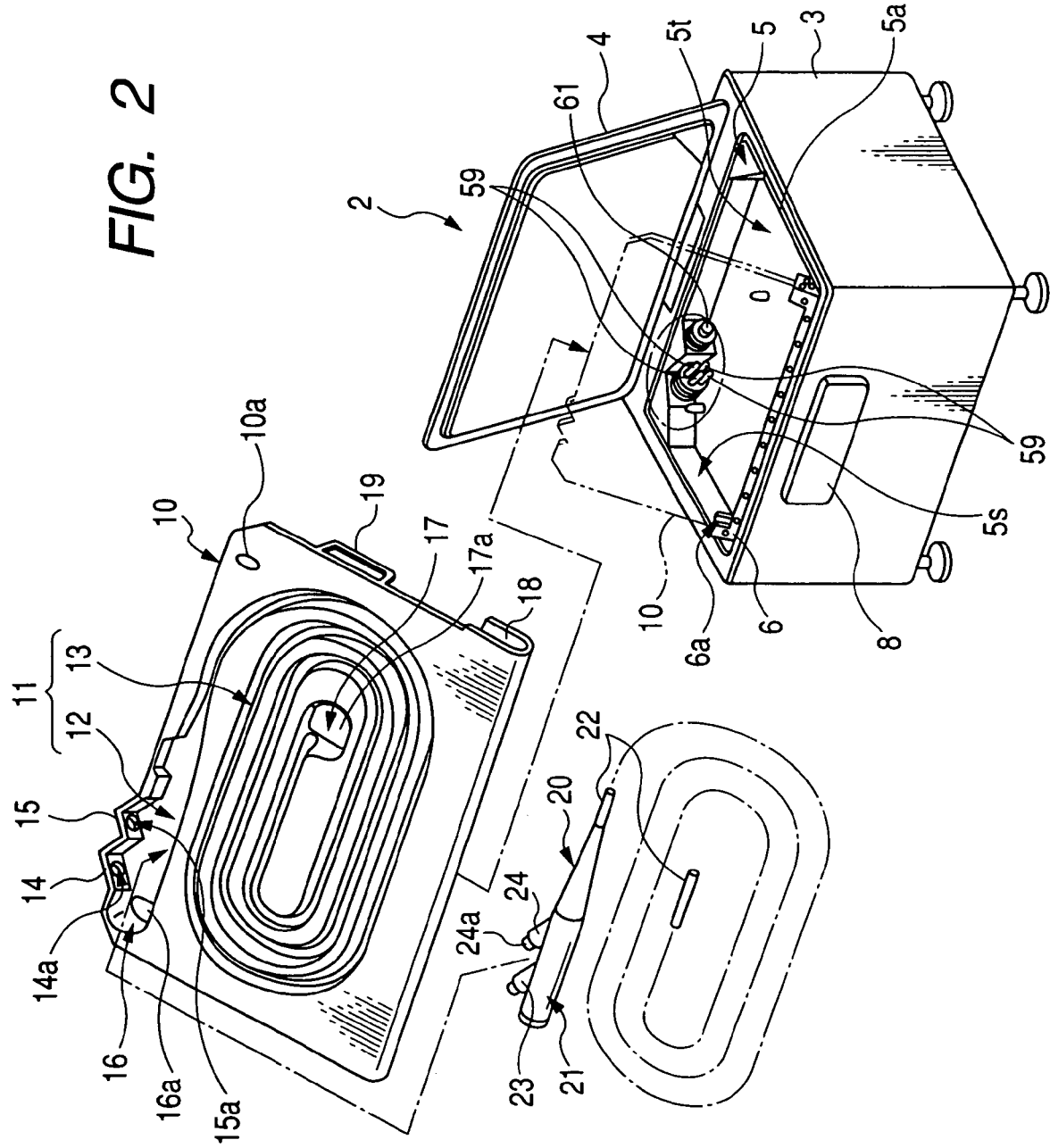
FIG. 2 is a perspective view showing an endoscope holder tray and an endoscope accommodated in a washing and disinfecting bath of the endoscope washing and disinfecting apparatus, shown in FIG. 1, and the endoscope washing and disinfecting apparatus with the top cover remaining in an opened state.

In FIGS. 1 and 2, a medical instrument washing and disinfecting apparatus of a first embodiment is described in terms of its overall configuration. The present embodiment will be described as applied to an endoscope washing and disinfecting apparatus serving as the medical instrument washing and disinfecting apparatus according to the present invention.

As shown in FIG. 1, the endoscope washing and disinfecting apparatus 2, playing a role as an apparatus washing and disinfecting a used endoscope 20 (see FIG. 2) and related therapeutic tools (instruments), comprises a major section that includes a washing and disinfecting apparatus body (hereinafter merely referred to as an apparatus body) 3 and top cover 4 coupled to an upper portion of the apparatus body 3 by means of hinges (see FIG. 3) for opening and closing capabilities.

Further, an upper area of the apparatus body 3 has a washing and disinfecting bath 5 having an upwardly opening endoscope reception opening, which is opened or closed with the top cover 4, and having a given depth. In addition, the washing and disinfecting bath 5 is universal for accommodating an endoscope 20 and an endoscope holding tray (hereinafter merely referred to as a tray) 10 (see FIG. 2).

Further, the apparatus body 3 has an upper area carrying a packing 5a disposed in a position surrounding the washing and disinfecting bath 5 to provide a watertight effect between the apparatus body 3 and the top cover 4 when the top cover 4 is moved down to close the apparatus body 3.

Furthermore, the apparatus body 3 has a front face, closer to, for instance, an operator, which carries thereon an operation panel 8 having various input operation switches such as, for instance, a washing and disinfection start switch for the apparatus body 3 and a washing and disinfection mode selection switch and display sections providing a display of washing and disinfecting time and a display of operational failure alarming or the like.

The top cover 4 is made of hard and optically transparent resin such as a so-called transparent resin member or half-transparent resin. Accordingly, even under a circumstance where the endoscope accommodation opening of the washing and disinfecting bath 5 remains in a closed state, an interior of the washing and disinfecting bath 5 can be visually observed through the top cover 4.

A tray holder member 6 is mounted on the washing and disinfecting bath 5, supported on the apparatus body 3, in a given position, that is, in a position closer to the operator and near the operation panel 8.

The tray holder member 6 takes the form of a structure having tilting and shifting capabilities by means of pivot pins in a mounting and decoupling position, obliquely oriented upward for mounting or demounting a tray 10, and an accommodating position, parallel to a bottom surface 5t of the washing and disinfecting bath 5, in which the tray 10 is accommodated in the washing and disinfecting bath 5.

A first opening and closing protrusion is provided on the bottom surface 5t of the washing and disinfecting bath 5 in a given position thereof, that is, in a position remote from the operator at an area closer to the hinge 4a. In addition, a water supply port 16c is provided in an area close proximity to the first opening and closing protrusion 7a. Moreover, a second opening and closing protrusion 7b is provided on the bottom surface 5t at a substantially central area thereof. In addition, a drain outlet 17c is provided in an area near the second opening and closing protrusion 7b.

With the tray 10 accommodated in the washing and disinfecting bath 5, the first opening and closing protrusion 7a depress a lid member 16a, which will be described below, of the tray 10 for the opening operation. The second opening and closing protrusion 7b depresses a lid member 17a, which will be described below, of the tray 10 for the opening operation.

The water supply port 16c serves to supply washing liquid, disinfecting liquid and flushing out water or the like into the washing and disinfecting bath 5. The drain outlet 17c drains washing liquid, disinfecting liquid and flushing out water or the like out of the washing and disinfecting bath 5.

The washing and disinfecting bath 5 has an outer periphery that has a side closer to, for instance, the operator for carrying a fluid duct fluid supply unit (hereinafter referred to as a first fluid supply unit) 50 and a therapeutic-tool insertion duct fluid supply unit (hereinafter referred to as a second fluid supply unit) 60.

The first fluid supply unit 50 is arranged to move away (protrude) from a sidewall 5s of the washing and disinfecting bath 5 or move closer to the sidewall 5s in a direction perpendicular thereto upon operation of a shift mechanism 91 (see FIG. 5) in a manner as will be described below. In addition, a detailed structure of the first fluid supply unit 50 is described below.

Further, the second fluid supply unit 60 has a distal end formed with a therapeutic-tool insertion duct supply nozzle 61 arranged to protrude from the sidewall 5s of the washing and disinfecting bath 5 into the washing and disinfecting bath 5.

As shown in FIG. 2, the tray holder member 6, provided on the washing and disinfecting bath 5 of the apparatus body 3, has a holder portion 6a that carries the tray 10, in which the used endoscope 20 or the like is accommodated, for mounting and demounting capabilities.

The endoscope 20, available to be freely mounted in or demounted from the tray 10, comprises a major section that includes a manipulator section 21 and a flexible inserting section 22 contiguous with the manipulator section 21. In addition, the manipulator section 21 and the flexible inserting section 22 internally have a forward water supply duct 71s (see FIG. 8), playing a role as a fluid duct for supplying water from an opening of the distal end of the inserting section 22 to a front area, and a water supply duct 72s (see FIG. 8) playing a role as a fluid duct to supply water from an opening placed in opposition to an objective lens.

The manipulator section 21 and the flexible inserting section 22 internally have a gas feed duct 73s (see FIG. 8), acting as a fluid duct for supplying air from an opening, formed in opposition to the objective lens, to a surface of the objective lens located at the distal end of the inserting section 22, and a therapeutic tool insertion duct (not shown) available for a therapeutic tool to project from the opening formed at the distal end of the flexible inserting section 22. In the present case, the air is used as the gas.

The manipulator section 21 has various attachments such as a cylindrical duct coupling section 23 and a therapeutic tool coupling section 24, both of which obliquely protrude toward a base portion of the manipulator section 21 in a direction opposite to the flexible inserting section 22 longitudinally extending from the manipulator section 21. In addition, the duct coupling section 23 and the therapeutic-tool coupling section 24 are distanced from each other along a longitudinal direction the manipulator section 21.

Figure 4:
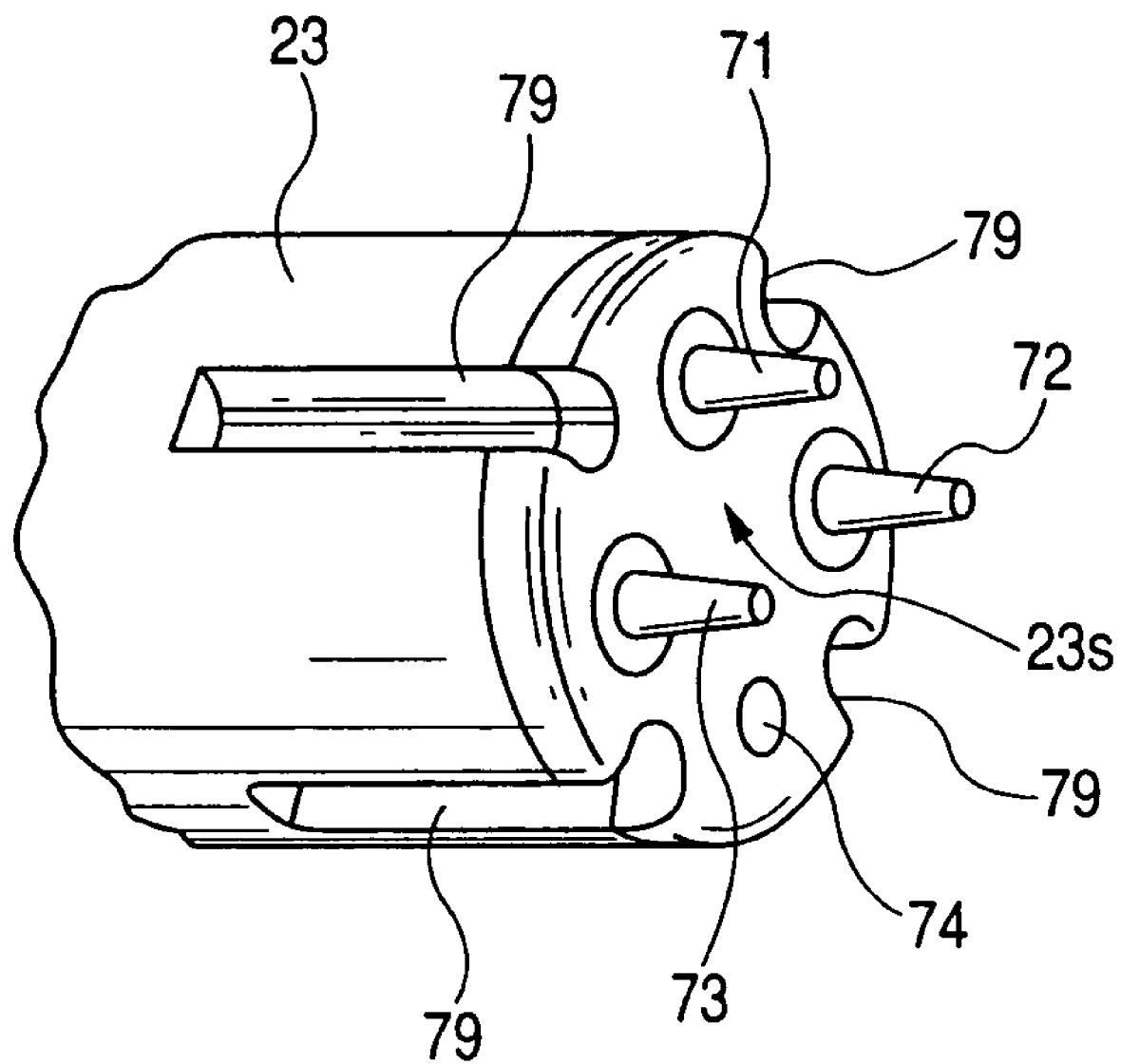
FIG. 4 is an enlarged perspective view showing a duct coupling section provided on a manipulator section of the endoscope shown in FIG. 2.

As shown in FIG. 4, the duct coupling section 23 has an apical surface 23s provided with a forward water supply duct fitting 71, acting as a fluid duct fitting formed with an opening through which the forward water supply duct 71s extends and which is oriented toward the manipulator section 21, a water supply duct fitting 72 acting as a fluid duct fitting formed with an opening through which the water supply duct 72s extends and which is oriented toward the manipulator section 21, and a gas supply duct fitting 73 acting as a fluid duct fitting formed with an opening through which the gas feed duct 73s extends and which is oriented toward the manipulator section 21. In addition, the apical surface 23s of the duct coupling section 23 has a water leakage detecting duct fitting 74 formed with an opening communicating with an inside of the endoscope 20.

Moreover, the forward water supply duct fitting 71, the water supply duct fitting 72, the gas supply duct fitting 73 and the water leakage detecting duct fitting 74 stand upright from the apical surface 23s in parallel to each other. In addition, an internal structure of the duct coupling section 23 will be described below in detail.

With the first fluid supply unit 50 coupled to the duct coupling section 23, the forward water supply duct fitting 71 is inserted to a forward water supply nozzle 51 (se FIG. 5), which will be described below, of the first fluid supply unit 50 and, in addition, the water supply duct fitting 72 is inserted to a water supply nozzle 52 (see FIG. 5), which will be described below, of the first fluid supply unit 50.

Further, with the first fluid supply unit 50 coupled to the duct coupling section 23, the gas supply duct fitting 73 is inserted to a gas supply nozzle 53 (see FIG. 5), described below, of the first fluid supply unit 50 to which with the first fluid supply unit 50 coupled to the duct coupling section 23, a water leakage detecting nozzle 54 (see FIG. 5), described below, of the first fluid supply unit 50 is also inserted.

The duct coupling section 23 has an outer circumferential periphery formed with four linear guide recesses 79 each of which axially extends from the apical surface 23s in a length half of the duct coupling section 23. With the first fluid supply unit 50 coupled to the duct coupling section 23, four guide pins 59, described below, of the first fluid supply unit 50 are slidably fitted to the four guide recesses 79, respectively.

The therapeutic-tool coupling section 24 has an apical surface provided with a therapeutic-tool insertion duct fitting 24a formed with an opening for communicating with the manipulator section 21 for the therapeutic-tool insertion duct. The therapeutic-tool insertion duct fitting 24a is connected to a therapeutic-tool insertion duct supply nozzle 61, provided on the second fluid supply unit 60 on a distal end thereof via for instance a tube or the like.

As shown in FIG. 2, the tray 10 has an upper surface formed with an accommodating concave section 11 adapted to accommodate and locate the endoscope 20 in a given position. The accommodating concave section 11 is formed in a given profile on consideration of external shapes and lengthwise dimensions of the manipulator section 20 and the inserting section 22 of the endoscope 20 to be accommodated and comprises a manipulator-section accommodating portion 12 and an inserting-section accommodating portion 13.

Accordingly, for using a plurality of kinds of endoscopes 20 having the manipulator sections 21 and the inserting sections 22 different in external shape and lengthwise dimension, a plurality of trays 10 are prepared to meet various kinds of endoscopes 20.

For the endoscope 20 to be accommodated in the accommodating concave section 11, the manipulator-section accommodating portion 12 has a pipe receiver section 14 and a therapeutic-tool receiver section 15 that accommodate the duct coupling section 23 and the therapeutic-tool coupling section 24 of the endoscope 20, respectively.

The pipe receiver section 14 is formed with an opening portion 14a to which a protruding distal end of the duct coupling section 23 is inserted. The therapeutic-tool receiver section 15 is formed with an opening portion 15a to which a protruding distal end of the therapeutic-tool coupling section 24 is inserted.

A first water supply and drainage port 16 is formed in the manipulator-section accommodating portion 12 on a bottom wall thereof at a given position for supplying and draining washing water and disinfecting water or the like. In addition, for the endoscope 20 to be accommodated in the accommodating concave section 11, the first water supply and drainage port 16 is located in an area close proximity to the base of the manipulator section 21 of the endoscope 20 while assuming a position in the vicinity of the water supply inlet 16c with the tray 10 being accommodated in the washing and disinfecting bath 5.

Further, a second water supply and drainage port 17 is formed in the manipulator-section accommodating portion 12 on the bottom wall at another given position thereof for supplying and draining washing water and disinfecting water or the like. In addition, with the endoscope 20 accommodated in the accommodating concave section 11, the second water supply and drainage port 17 is located in an area close proximity to a distal end of the inserting section 22 of the endoscope 20 while assuming a position in the vicinity of a water drain outlet 17c with the tray 10 being accommodated in the washing and disinfecting bath 5.

Furthermore, the first and second water supply and drainage ports 16, 17 have lid members 16a, 17a mounted for opening and closing capabilities, respectively. The lid members 16a, 17a take the form of structures that are normally kept under closed conditions, respectively, with own weights and additional biasing forces exerted by biasing means (not shown).

Consequently, when the used endoscope 20 is accommodated in the accommodating concave section 11, no contaminant or body fluid, adhered onto the endoscope 20, is leaked from the first and second water supply and drainage ports 16, 17. Therefore, the endoscope 20 can be hygienically conveyed with the endoscope 20 accommodated in the accommodating concave section 11 of the tray 10.

A mounting portion 18 is formed on the tray 10 on one sidewall thereof and extends in a direction so as to intersect a longitudinal direction in FIG. 2. When accommodating the tray 10 in the washing and disinfecting bath 5 of the apparatus body 3, the mounting portion 18 is fitted to the holder portion 6a of the tray holder member 6, provided in the washing and disinfecting bath 5, and is formed in a shape, for instance, a U-shaped configuration in conformity to an internal profile of the holder portion 6a.

Carrier grips 19 are formed on the tray 10 on both sides thereof at areas distanced along the longitudinal direction in FIG. 2. The carrier grips 19, available to be gripped when carrying the tray 10 accommodated with the endoscope 20, are formed so as to protrude downward from the tray 10. Therefore, no interference takes place between the carrier grips 19 and the top cover 4 with the tray 10 being accommodated in the washing and disinfecting bath 5.

A wireless IC tag 10a is formed on the upper surface of the tray 10. The wireless IC tag 10a is registered with identification data indicative of a type of the endoscope 20 accommodated and placed in the accommodating concave section 11 of the tray 10.

With such a structure, during a phase in which the endoscope 20 is accommodated and located in the accommodating concave section 11 of the tray 10, the inserting section 22 is accommodated and located in the inserting-section accommodating portion 13 and a distal end of the duct coupling section 23 of the manipulator section 21 is inserted to the opening portion 14a of the pipe receiver section 14. In addition, the distal end of the therapeutic-tool coupling section 24 is inserted to the opening portion 15a of the instrument-tool receiver section 15. This results in a consequence wherein the duct coupling section 23 and the therapeutic-tool coupling section 24 are positioned and located in the manipulator-section accommodating portion 12 at a given position.

More particularly, with the tray 10 being accommodated in the washing and disinfecting bath 5, the tray 10 is set down such that a position of the duct coupling section 23 is defined to fall in a face-to-face relation to the first fluid supply unit 50 and a position of the therapeutic-tool coupling section 24 is defined to fall in a face-to-face relation to the second fluid supply unit 60.

After the endoscope 20 has been accommodated in the accommodating concave section 11, the tray 10 is held in engagement with the tray holder member 6 that can be located in mounting and decoupling positions as shown by a phantom line as shown in FIG. 2. At this moment, the mounting portion 18 of the tray 10 is fitted to the holder portion 6a of the tray holder member 6. Subsequently, by turning the tray holder member 6 from the decoupling position to an accommodating position into the washing and disinfecting bath 5 in a manual or automatic manner, the tray 10 located on the tray holder member 6 is received in the washing and disinfecting bath 5 at a given position thereof as shown in FIG. 3 with the turning movement of the tray holder member 6.

Thereafter, the first opening and closing protrusion 7a, standing upright from the bottom wall 5t of the washing and disinfecting bath 5, lifts up the lid member 16a thereby opening the first water supply and drainage port 16. Meanwhile, the second opening and closing protrusion 7b operates to lift up the lid member 17a thereby opening the second water supply and drainage port 17.

Figure 3:
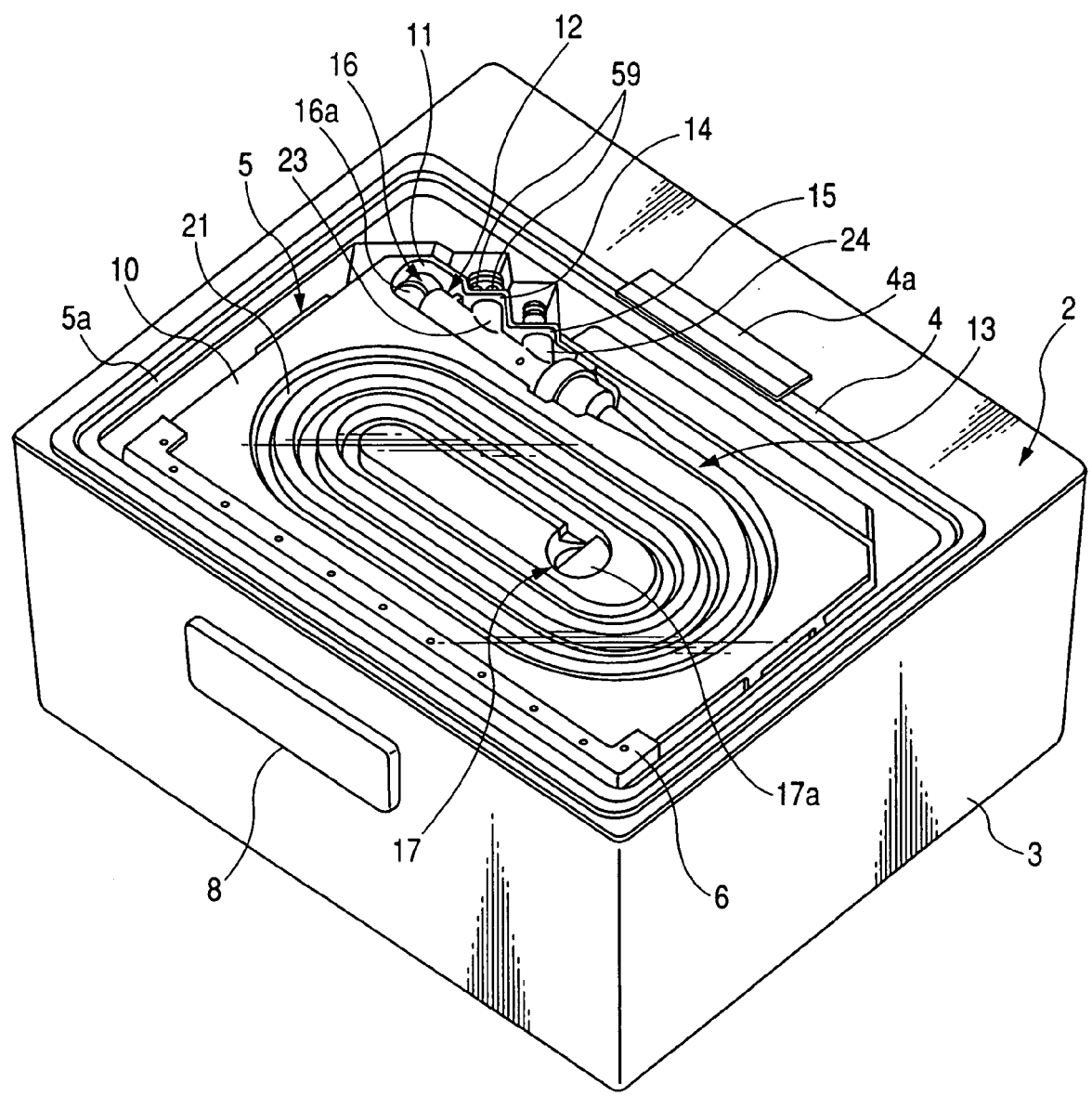
FIG. 3 is a perspective view showing the endoscope, accommodated in the endoscope holder tray shown in FIG. 2, is accommodated in the washing and disinfecting bath of the endoscope washing and disinfecting apparatus, shown in FIG. 1, with the top cover being closed.

As shown in FIG. 3, further, the position of the duct coupling section 23 is placed in opposition to the first fluid supply unit 50. Meanwhile, the position of the therapeutic-tool coupling section 24 is placed in opposition to the second fluid supply unit 60.

Thereafter, the top cover 4 is manually or automatically moved in a closing direction, thereby closing the endoscope receiver opening of the washing and disinfecting bath 5. When this takes place, the packing 5a, disposed in the apparatus body 3 on the upper surface thereof, allows the top cover 4 and the apparatus body 3 to be kept watertight. Thus, no liquid is caused to scatter from the washing and disinfecting bath 5 to the outside of the apparatus body 3 during washing and disinfecting operations.

The structure of the first fluid supply unit 50 will now be described below in detail with reference to FIGS. 1 to 4 and FIGS. 5 to 8.

Figure 5:
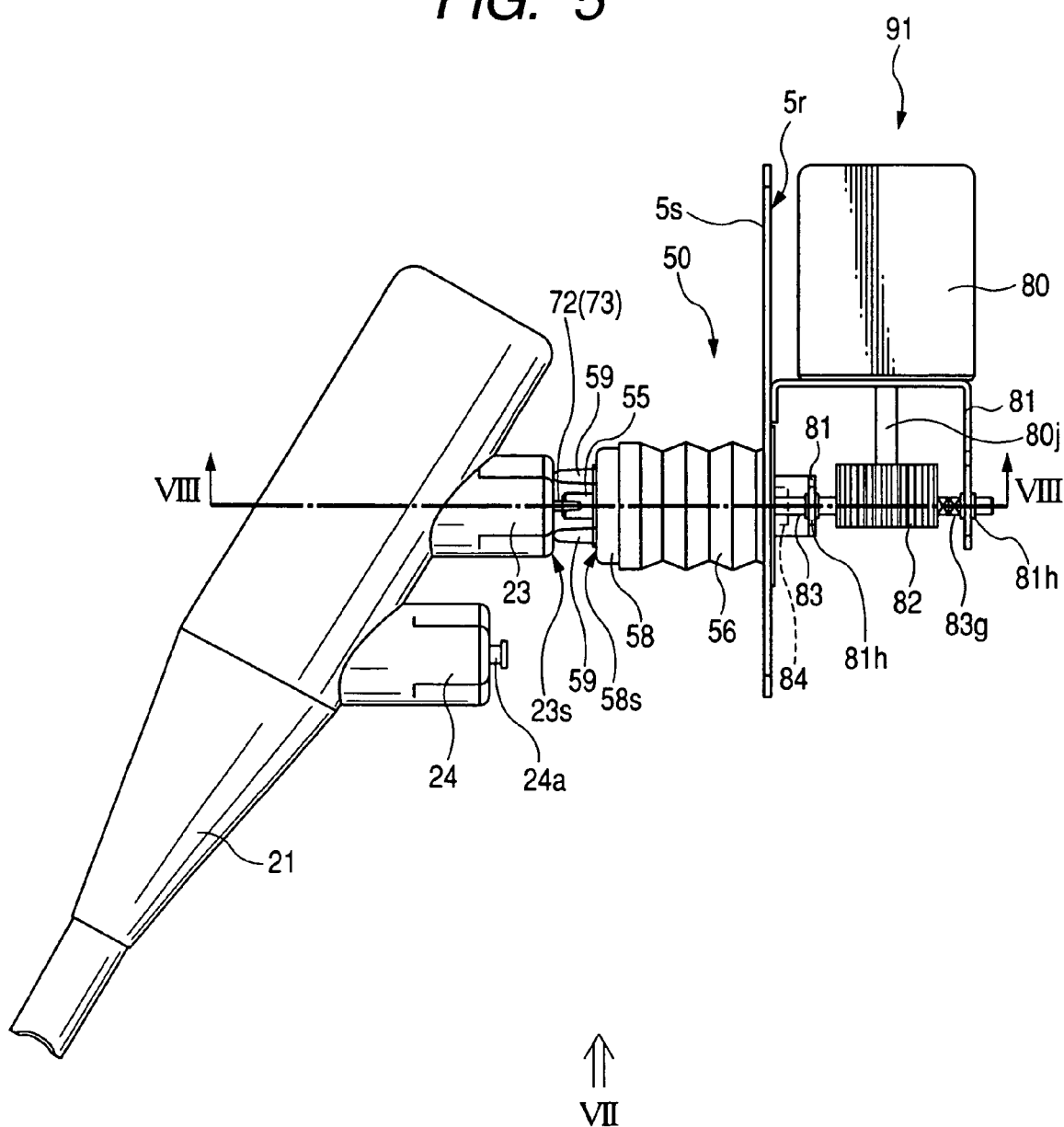
FIG. 5 is a plan view showing a structure of a first fluid supply unit, shown in FIG. 1, a shift mechanism of the unit and the manipulator of the endoscope.

As shown in FIG. 3, when the tray 10 with the endoscope 20 being accommodated therein is placed in the washing and disinfecting bath 5 of the apparatus body 3, the duct coupling section 23 of the manipulator section 21 forming part of the endoscope 20 is placed in face-to-face relation to the first fluid supply unit 50 as shown in FIG. 5. More particularly, the apical surface 23s of the duct coupling section 23 is placed in face-to-face relation to an apical surface 58s of a distal end 58 of the first fluid supply unit 50 as shown in FIGS. 5 and 7.

Figure 7:
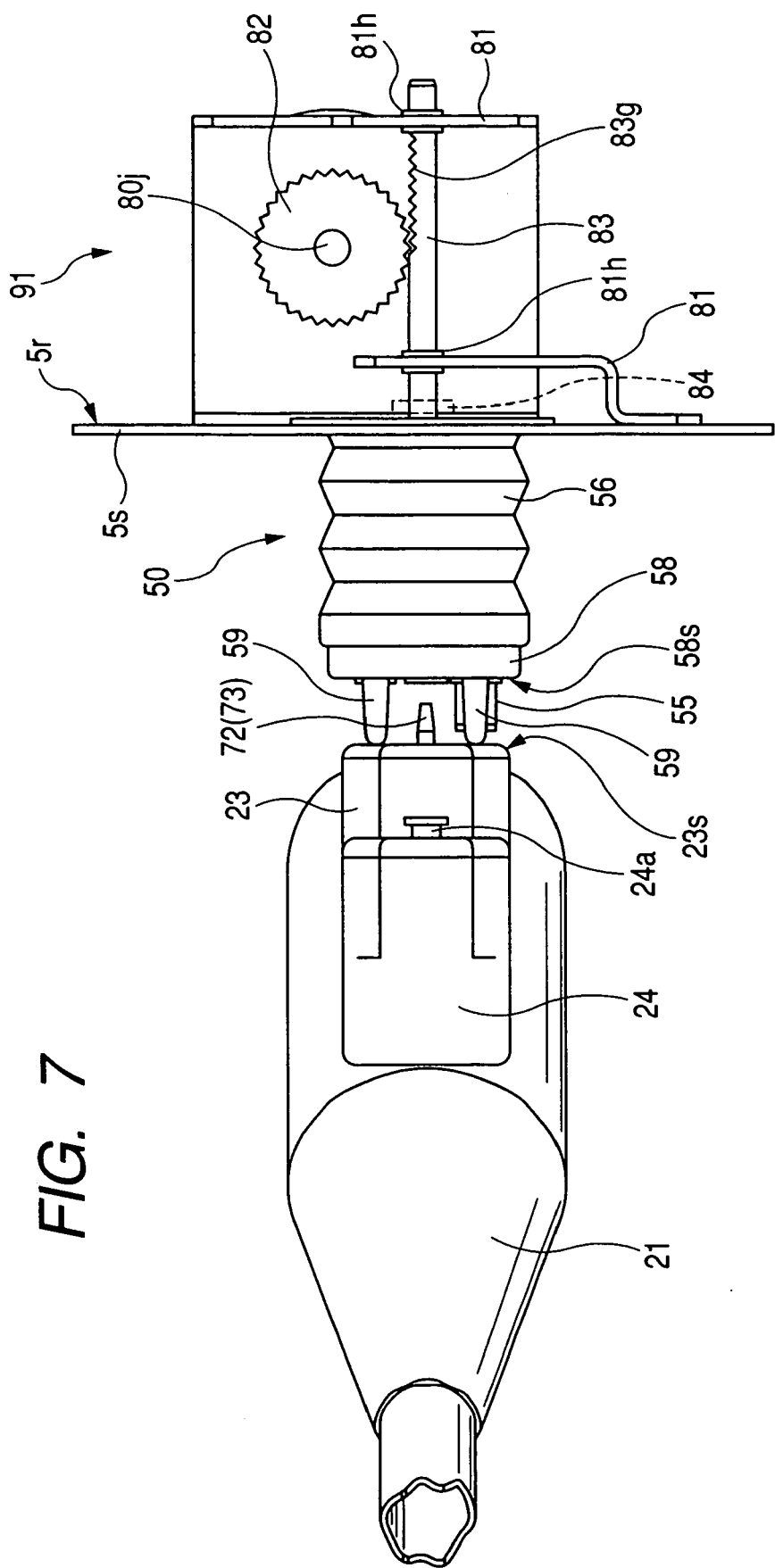
FIG. 7 is a plan view of the first fluid supply unit, shown in FIG. 5, the shift mechanism of the unit and the manipulator of the endoscope as viewed in a direction VII.
Figure 8:
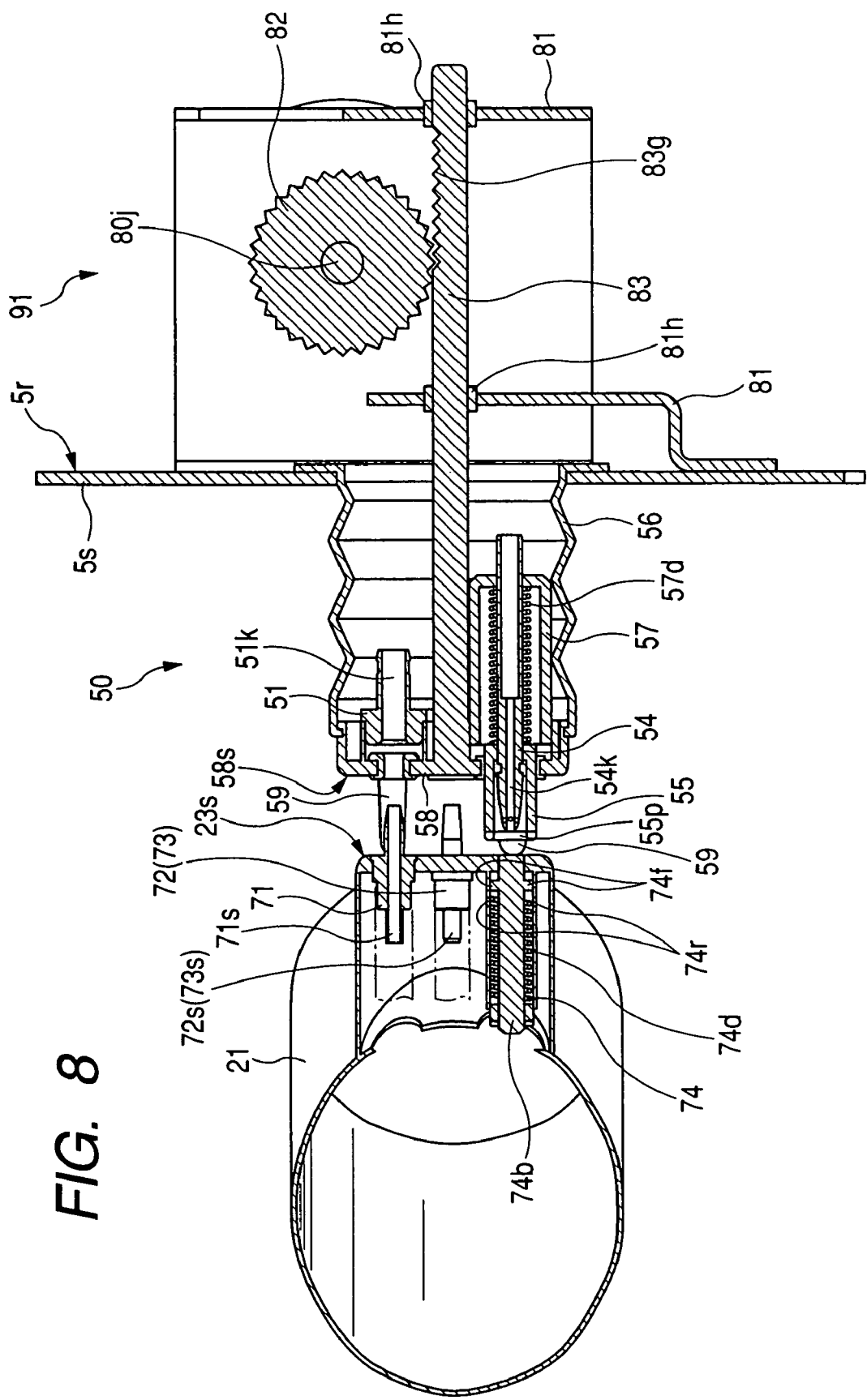
FIG. 8 is a cross sectional view taken on line VIII-VIII of FIG. 5.

As shown in FIGS. 5, 7 and 8, the first fluid supply unit 50 comprises a major section that includes an axial rod 83 extending through a sidewall 5s in a direction perpendicular thereto so as to protrude into the washing and disinfecting bath 5, a disc-like toughened distal end portion 58 contiguously provided a distal end of the axial rod 83 in a position inside the washing and disinfecting bath 5, and a cylindrical accordion-like member 56, made of for instance a rubber member, which has a distal end, fixedly secured to an outer periphery of the distal end 58, and a base portion connected to the sidewall 5s of the washing and disinfecting bath 5.

Further, the first fluid supply unit 50 is fixedly secured to the sidewall 5s such that accordion-like member 56 protrudes into the washing and disinfecting bath 5 in a direction perpendicular to the sidewall 5s.

In particular, the sidewall 5s has a backside 5r, supporting thereon the first fluid supply unit 50, to which a support member 81 is fixedly secured to fixedly support the first fluid supply unit 50 to the sidewall 5s and forms the shift mechanism 91.

The support member 81 has two through-bores 81h, sized in the substantially same diameter as an outer diameter of the axial rod 83, which rotatably support an intermediate portion, placed in a position near the backside 5r, and a base portion, located in an inside of the sidewall 5s, of the axial rod 83, under which the first fluid supply unit 5 is supported.

Further, a motor 80, forming part of the shift mechanism 91, is fixedly mounted on the support member 81 so as to allow a motor gear 82, provided on a distal end of a rotary shaft 80j extending from the motor 80, to be held in meshing engagement with a feed gear 83g formed on the base portion of the axial rod 83. In addition, a controller 1 (see FIG. 9) executes motion control to drive the motor 80 in a manner as will be described below.

Figure 10:
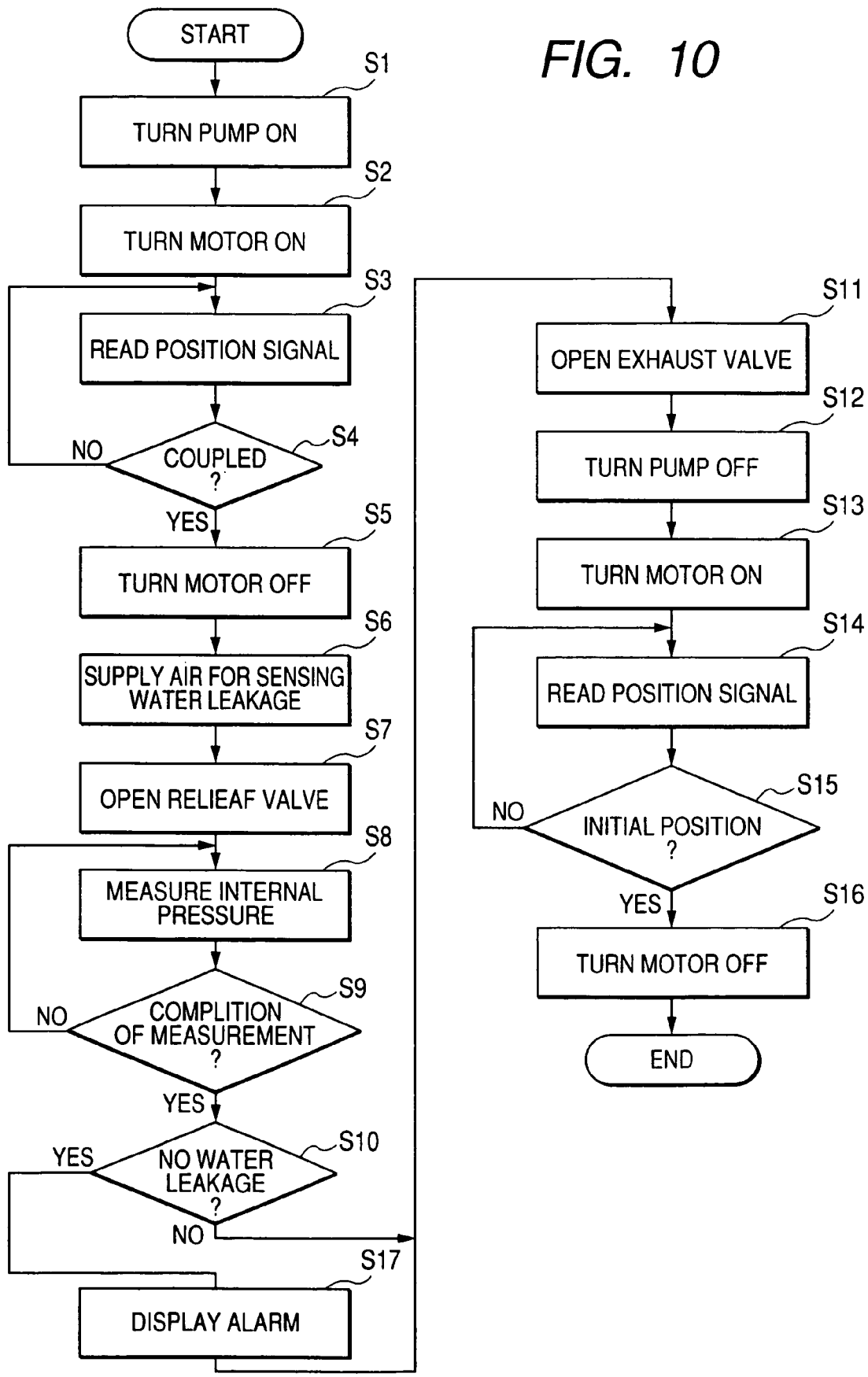
FIG. 10 is a flow chart illustrating a basic sequence of operations of the endoscope washing and disinfecting apparatus shown in FIG. 1.

The controller 1 is formed as, by way of example, a computer system equipped with a CPU (central processing unit) and memories (not shown) and operative based on programs previously stored in a memory. One example of the operations of the controller 1 is shown in FIG. 10 described later.

With such a structure described above, as the motor 80 is energized to rotate in one direction, the output torque of the motor 80 is transferred from the motor gear 82, meshing with the feed gear 83g, to the axial rod 83 for conversion to a drive force so as to allow the axial rod 83 to protrude into the washing and disinfecting bath 5 in a direction perpendicular to the sidewall 5s as shown in FIG. 7.

With the motor 80 rotated in a reverse direction opposite to the one direction, the output torque of the motor 80 reversely acts on the axial rod 83 through the motor gear 82, meshing with the feed gear 83g, to retract the same into an area inward of the sidewall 5s in a direction perpendicular thereto.

That is, as the motor 80 rotates, the first fluid supply unit 50 moves in a direction closer to or away from the sidewall 5s in a direction perpendicular thereto. More particularly, the first fluid supply unit 50 moves in a coupling position closer to or an uncoupling position away from the duct coupling section 23 integrally formed on the manipulator section 21 of the endoscope 20 set in the washing and disinfecting bath 5.

A position sensor 84 is mounted on the support member 81 for detecting a position of the axial rod 83. The position sensor 84 serves to detect the position of the axial rod 83, that is, a position of the first fluid supply unit 50 and transmits the resulting detection result to the control means (see FIG. 9) for enabling feedback control of the rotation of the motor 80.

Figure 6:
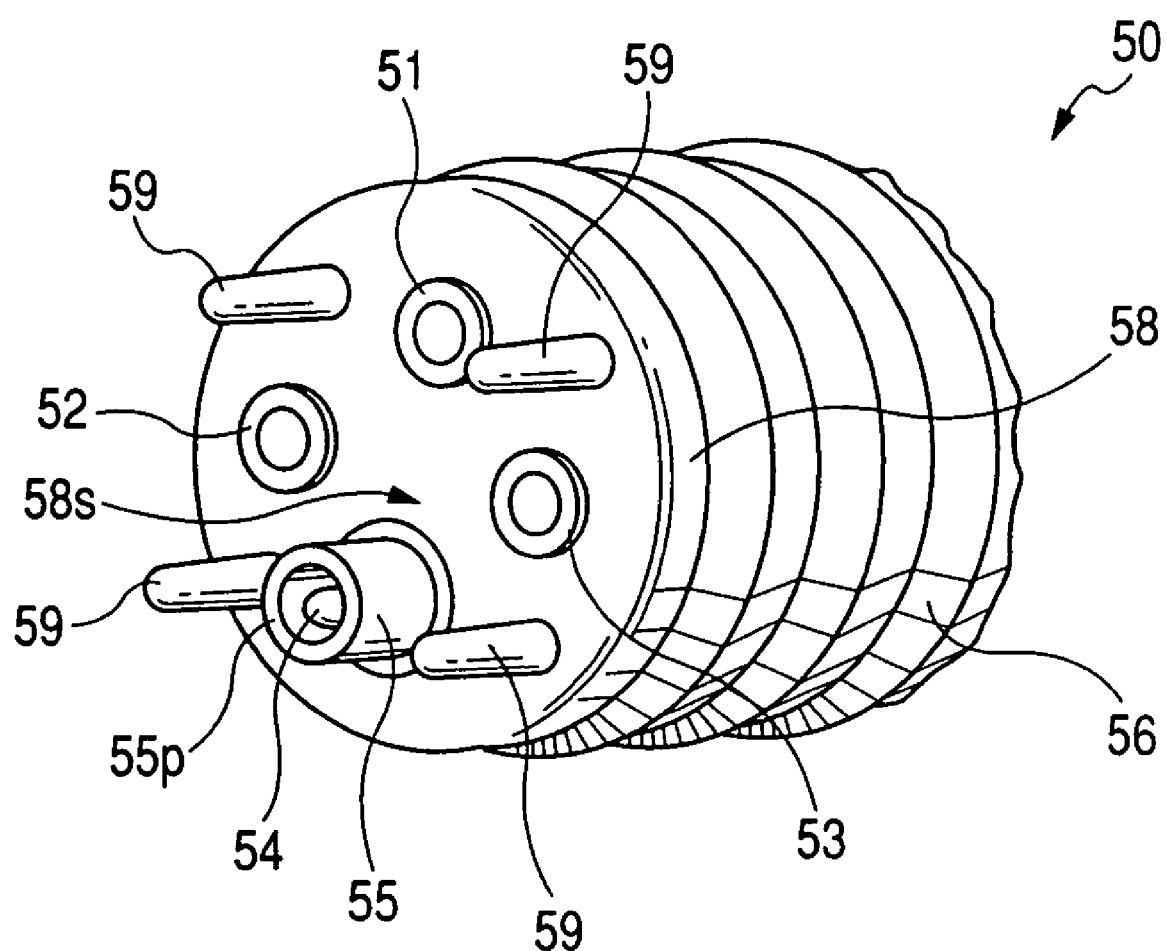
FIG. 6 is an enlarged perspective view of the first fluid supply unit shown in FIG. 5.

As shown in FIG. 6, the first fluid supply unit 50 has a distal end 58 whose apical surface 58s is formed with four guide pins 59 protruding in a direction perpendicular to the apical surface 58s in parallel to each other.

During operation of the motor 80 to shift the first fluid supply unit 50 such that the first fluid supply unit 50 is coupled to the duct coupling section 23 of the endoscope 20, the four guide pins 59 are caused to slidably fitted to the four guide recesses 79 formed on the outer periphery of the coupling section 23, thereby guiding the first fluid supply unit 50 into engagement with the duct coupling section 23.

The first fluid supply unit 50 internally has the forward water supply nozzle 51 playing a role as a fluid supply nozzle, the water supply nozzle 52 playing a role as a fluid supply nozzle, the gas supply nozzle 53 playing a role as a fluid supply nozzle, and the water leakage detecting nozzle 54, which are opened on the same plane in parallel to each other.

That is, the forward water supply nozzle 51, the water supply nozzle 52, the gas supply nozzle 53 and the water leakage detecting nozzle 54 are oriented in the same connecting direction. In addition, the respective nozzles 51 to 54 extend through the distal end portion 58.

Further, the forward water supply nozzle 51 is formed in coaxial relation to the forward water supply duct fitting 71 and the water supply nozzle 52 is formed with the water supply duct fitting 72 in coaxial relation thereto. Meanwhile, the gas supply nozzle 53 is formed in coaxial relation to the gas supply duct fitting 73 and the water leakage detecting nozzle 54 is formed in coaxial relation to the water leakage detecting duct fitting 74.

The forward water supply nozzle 51 is connected to an outer periphery of a duct 51k, branched off from a common duct (see FIG. 9) having one end connected to a stirring bath 32 described below as shown in FIG. 8 and, as shown in FIG. 6, the forward water supply nozzle 51 has an opening formed in a position slightly protruding from the apical surface 58s of the distal end 58.

Figure 11:
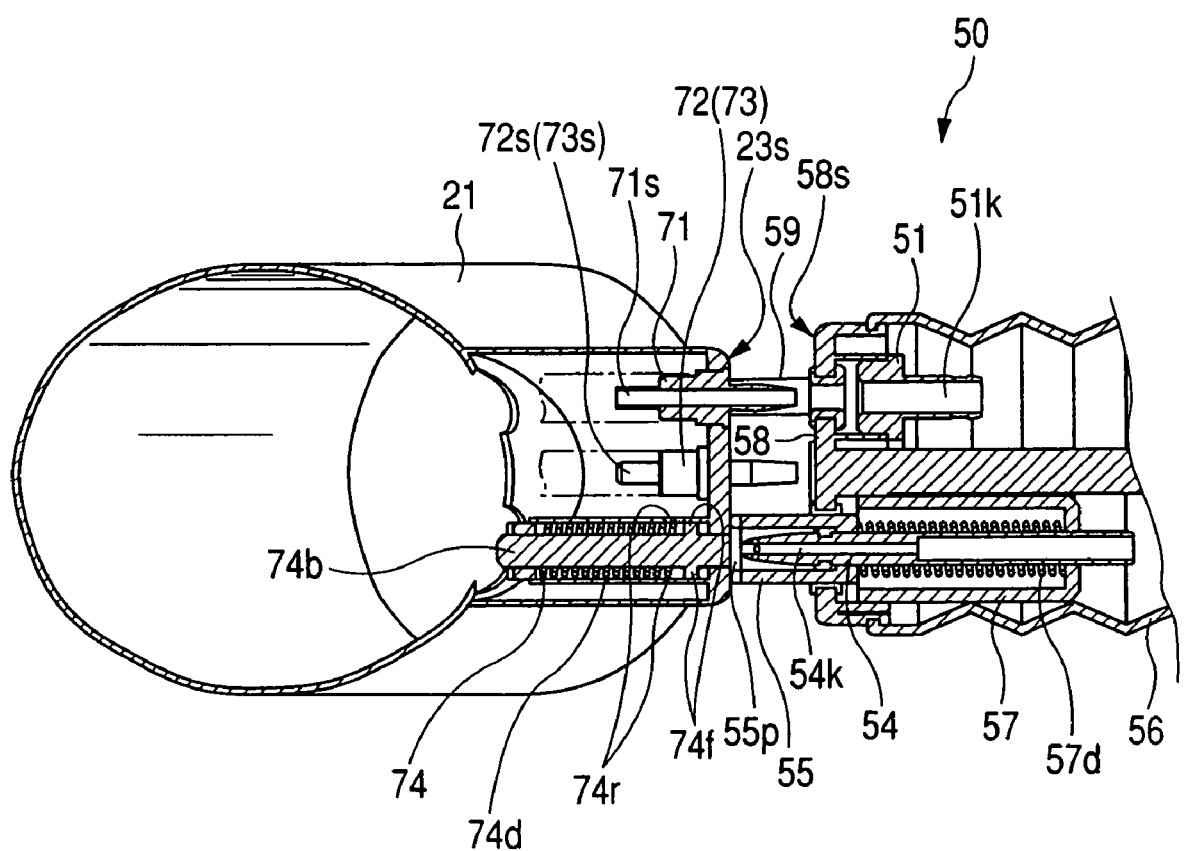
FIG. 11 is a cross sectional view showing the first fluid supply unit, the shift mechanism and the manipulator section of the endoscope for illustrating an initial status with the first fluid supply unit, shown in FIG. 5, being coupled to the duct coupling section.

In addition, with the first fluid supply unit 50 coupled to the duct coupling section 23, the forward water supply nozzle 51 is connected such that a distal end of a forward water supply duct 71s, formed in the forward water supply duct fitting 71 of the duct coupling section 23, is inserted to the duct 51k in a manner as shown in FIG. 11 that will be explained below.

The water supply nozzle 52 is connected to an outer periphery of a duct (not shown), branched off from the common duct (see FIG. 9) whose one ed is connected to the stirring bath 32 described below and, as shown in FIG. 6, the water supply nozzle 52 has an opening formed in a position slightly protruding from the apical surface 58s of the distal end 58.

In addition, with the first fluid supply unit 50 coupled to the duct coupling section 23, the water supply nozzle 52 is connected such that a distal end of the water supply pipe 72s, formed in the water supply duct fitting 72 of the duct coupling section 23, is inserted to an inside of the water supply nozzle 52.

The gas supply nozzle 53 is connected to an outer periphery of a duct (not shown), branched off from the common duct (see FIG. 9) whose one ed is connected to the stirring bath 32 described below and, as shown in FIG. 6, the gas supply nozzle 53 has an opening formed in a position slightly protruding from the apical surface 5s of the distal end 58.

In addition, with the first fluid supply unit 50 coupled to the duct coupling section 23, the gas supply nozzle 53 is connected such that a distal end of the air supply pipe 73s, formed in the gas supply duct fitting 73 of the duct coupling section 23, is inserted to an inside of the gas supply nozzle 53.

The water leakage detecting nozzle 54 is connected to an outer periphery of a duct (not shown), branched off from the common duct (see FIG. 9) whose one ed is connected to the stirring bath 32 described below as shown in FIG. 8 and the water leakage detecting nozzle 54 has a distal end protruding from the apical surface 58s of the distal end 58 in a direction perpendicular thereto.

In addition, the pipe 54k of the water leakage detecting nozzle 54 has a distal end and sidewall branched off in three ways. Moreover, with the first fluid supply unit 50 coupled to the duct coupling section 23, the water leakage detecting nozzle 54 is connected such that the water leakage detecting nozzle 54 is inserted to an inside of the water leakage detecting duct fitting 74 of the duct coupling section 23.

The water leakage detecting duct fitting 74 is bottomed in shape as shown in FIG. 8 and has an inside receiving a coil spring 74d through which a valve body 74b, formed with a flange 74f, extends. In addition, the flange 74f is fitted to an inside of the coil spring 74d. Moreover, the water leakage detecting duct fitting 74 is formed with communication apertures 74r communicating with an inside of the endoscope 20.

The valve body 74b is structured such that the flange 74f remains in a position away from the communication apertures 74r to be closer to the apical surface 23s under a normal state to remain in a closed state and is opened only when the water leakage detecting nozzle 54 is inserted to the water leakage detecting duct fitting 74 to cause the flange 74f of the valve body 74b to be depressed toward a bottomed wall of the water leakage detecting duct fitting 74.

That is, with the water leakage detecting nozzle 54 inserted to the water leakage detecting duct fitting 74, the valve body 74b is opened to provide communication between the pipe 54k of the water leakage detecting nozzle 54 and the inside of the endoscope 20.

Further, the first fluid supply unit 50 internally has a sleeve member 55, extending in coaxial relation to the water leakage detecting nozzle 54 protruding from the apical surface 58s and surrounding an outer periphery of the water leakage detecting nozzle 54, which is disposed in the inside of the first fluid supply unit 50 for protruding and retracting capabilities.

A concaved sleeve-member support member 57 is located in the first fluid supply unit 50 and accommodates therein a coil spring 57d with which a bottom portion of the sleeve member 55 is pivotally supported. In addition, the water leakage detecting nozzle 54 is inserted to an inside of the coil spring 57d.

Further, a packing 55p is provided on the sleeve member 55 on a distal end thereof. With the first fluid supply unit 50 coupled to the duct coupling section 23, the packing 55p is brought into abutting engagement with the apical surface 23s of the duct coupling section 23 covering the outer periphery of the water leakage detecting duct fitting 74 to tightly close the water leakage detecting duct fitting 74 and the sleeve member 55 in a watertight relationship.

The sleeve member 55 is normally pressed by the action of the coil spring 57d and protrudes from the apical surface 58s so as to cover the outer periphery of the water leakage detecting nozzle 54. Only when the water leakage detecting nozzle 54 is inserted to the water leakage detecting duct fitting 74, the bottom portion presses the coil spring 57d and is retracted into the first fluid supply unit 50, that is, retracted into the concaved sleeve-member support member 57.

Figure 9:
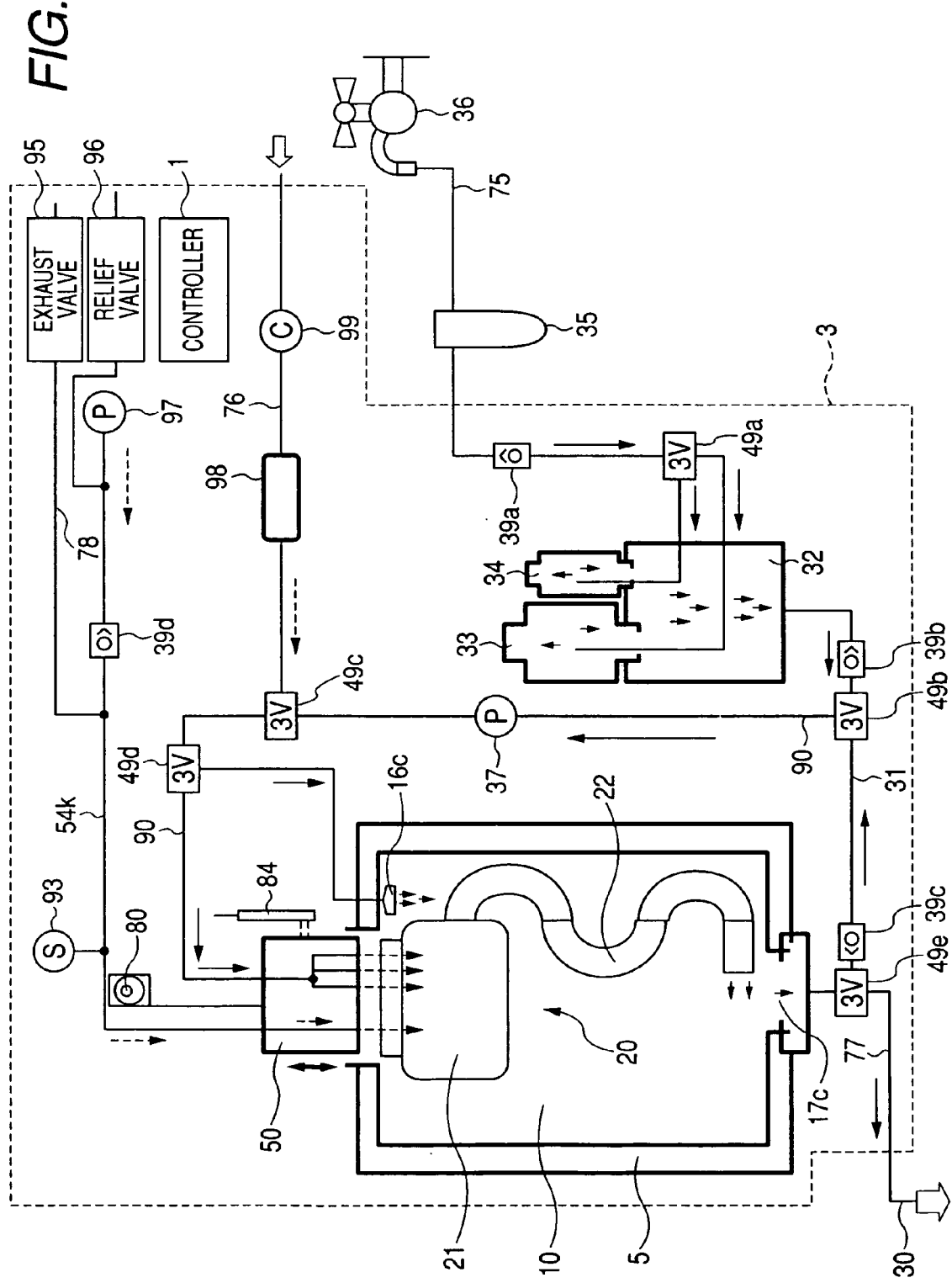
FIG. 9 is a schematic view showing a structure of an apparatus body of the endoscope washing and disinfecting apparatus shown in FIG. 1.

Now, an internal structure of the endoscope washing and disinfecting apparatus 2 with such a structure is described below with reference to FIG. 9. FIG. 9 is a view showing an outline of an overall structure of the endoscope washing and disinfecting apparatus shown in FIG. 1.

As shown in FIG. 9, a faucet 36, located outside the endoscope washing and disinfecting apparatus 2 for supplying tap water as dilution circulating liquid, is connected to a disinfectant bottle 33, storing therein disinfectant liquid, and a detergent bottle 34, storing therein detergent, both of which are set onto the stirring bath 32, via a duct 75. The stirring bath 32 is supplied with tap water by which disinfectant or detergent is diluted at a given concentration and stirred. Also, detergent diluted with water is hereinafter referred to as washing liquid.

The stirring bath 32 is connected to the respective nozzles 51 to 53 of the first fluid supply unit 50 via the common duct 90. The stirring bath 32 is sequentially connected to a check valve 39b, a three-way valve 49b, a washing and disinfecting pump 37, a three-way valve 49c and a three-way valve 49d in this order via the common duct 90. Although not shown, the common duct 90 is also connected to a therapeutic-tool insertion duct supplying nozzle 61 of the second fluid supply unit 60.

The check valve 39b serves to prevent back-flow of disinfecting liquid or washing liquid. Moreover, the three-way valve 49b plays a role as a valve, controllably operated by the controller 1, which switches over between disinfecting liquid or washing liquid, supplied from a circulation duct 31 described below, and disinfecting liquid or washing liquid supplied from the stirring bath 32 to allow selected liquid to flow through the common duct 90.

The washing and disinfecting pump 37 plays a role as a pump, controllably operated by the controller 1, which draws disinfecting liquid or washing liquid from the stirring bath 32 or the circulation duct 31 to supply given liquid to the respective nozzles 51 to 53 of the first fluid supply unit 50 or the water supply inlet 16c.

A compressor 99 is connected through a duct 76 to the three-way valve 49c to supply gas thereto. In addition, the duct 76 has a midway area in which an air filter 98 is disposed.

The three-way valve 49c plays a role as a valve, controllably operated by the controller 1, which selectively switches over an air stream, delivered from the compressor 99 via the duct 76, and disinfecting liquid or washing liquid, drawn by the washing and disinfecting pump 37 from the stirring bath 32 or the circulation duct 31, for supply to the respective nozzles 51 to 53 of the first fluid supply unit 50 or the water supply inlet 16c.

The three-way valve 49d plays a role as a valve, controllably operated by the controller 1, which selectively switches over the air stream, delivered from the compressor 99 via the duct 76, and disinfecting liquid or washing liquid, drawn by the washing and disinfecting pump 37 from the stirring bath 32 or the circulation duct 31, for supply to the respective nozzles 51 to 53 of the first fluid supply unit 50 or the water supply inlet 16c.

The drain outlet 17c, provided on the washing and disinfecting bath 5 at the bottom wall 5t thereof, is connected through the circulation duct 31 to the common duct 90. The circulation duct 31 has a midway area in which the three-way valve 49e and the check valve 39c are disposed in order from the drain outlet 17c.

Connected to the three-way valve 49e is a drain duct 77 that communicates with a drain 30. The three-way valve 49e plays a role as a valve, controllably operated by the controller 1, which switches disinfecting liquid or washing liquid, drained from the drain outlet 17c, for supply to the drain duct 77 or the circulation duct 31.

Further, disinfecting liquid or washing liquid, drained to the drain duct 77, is drained from the drain 30 to the outside of the apparatus body 3. Meanwhile, the washing and disinfecting pump 37 draws disinfecting liquid or washing liquid, fed to the circulation duct 31, through the common duct 90 for supply to the respective nozzles 51 to 53 or the water supply inlet 16c.

The apparatus body 3 incorporates therein a leaked water detecting pump 97, which is connected to the water leakage detecting nozzle 54 through the duct 54k. Connected to the duct 54k is a leaked water detecting sensor 93, an exhaust valve 95, a check valve 39d and a relief valve 96 in this order from the water leakage detecting nozzle 54.

The leaked water detecting pump 97 plays a role as a liquid supply means, controllably operated by the controller 1, which supplies gas such as air or the like to the water leakage detecting nozzle 54.

Under circumstances where the first fluid supply unit 50 is coupled to the duct coupling section 23 to allow the water leakage detecting nozzle 54 to be inserted to the water leakage detecting duct fitting 74 to open the valve body 74b for providing fluid communication between the duct 54k an the interior of the endoscope 20, the leaked water detecting sensor 93 plays a role as a sensor to measure an internal pressure of the duct 54k to detect whether or not a water-leaked area is created in side the endoscope 20.

The exhaust valve 95 plays a role as a valve, controllably operated by the controller 1, which upon completion of checking water leakage, allows air to be exhausted from the inside of the endoscope 20 via the duct 54k and an exhaust duct 78. In addition, the check valve 39d serves to prevent the back-flow of exhaust air delivered from the leaked water detecting pump 97.

Further, under circumstances where the first fluid supply unit 50 is coupled to the duct coupling section 23 to allow a given volume of air to be supplied to the inside of the endoscope 20, the relief valve 96 plays a role as a valve, controllably operated by the controller 1, which expels air to the outside without supplying air, fed from the leaked water detecting pump 97, to the duct 54k so as to prevent the supply of air with a volume greater than the given volume to the inside of the endoscope 20. Meanwhile, with water leakage being completely checked, the relief valve 96 permits air to be exhausted from the exhaust duct 78 while blocking the supply of air, delivered from the leaked water detecting pump 97, to the duct 54k for exhausting to the outside.

The operation of the endoscope washing and disinfecting apparatus 2 formed in such a structure will now be described below with reference to FIGS. 1 to 9 and FIGS. 10 to 12.

In addition, the operation of the endoscope washing and disinfecting apparatus 2 will now be described with reference to only leaked water detecting step for checking whether or not a water leakage area is created inside the endoscope 20.

First, the endoscope 20 is accommodated in the accommodating concave section 11, as described above, and the tray 10 is accommodated in the washing and disinfecting bath 5 as described above. Meanwhile, the duct coupling section 23 is located in face-to-face relation to the first fluid supply unit 50 and the therapeutic-tool coupling section 24 is located in face-to-face relation to the second fluid supply unit 60. Under such circumstances, the therapeutic-tool coupling section 24 and the therapeutic-tool insertion duct supply nozzle of the second fluid supply unit 60 are connected to each other through tubes or the like. Subsequently, the top cover 4 is manually or automatically moved in a closing direction, thereby closing the endoscope receiver opening of the washing and disinfecting bath 5 as shown in FIG. 3.

Then, in step S1 shown in FIG. 1, the controller 1 (FIG. 9) executes operation control such that the leaked water detecting pump 97 (FIG. 9) is turned on. Thus, the leaked water detecting pump 97 supplies air to the duct 54k, thereby causing air to be ejected from the opening of the water leakage detecting nozzle 54 of the first fluid supply unit 50.

In next step 52, the controller 1 executes operation control so as to turn on the motor 80. With the motor 80 turned on to rotate the rotary shaft 80j of the motor 80 in one direction, the motor gear 82 is caused to rotate in meshing engagement with the feed gear 83g of the axial rod 83. This causes the axial rod 83 to move in a direction perpendicular to the sidewall 5s to protrude into the washing and disinfecting bath 5. Meanwhile, the first fluid supply unit 50 is caused to move toward the duct coupling section 23 in the direction perpendicular to the sidewall 5s.

When this takes place, the position sensor 84 detects a shifted position of the first fluid supply unit 50 to allow the resulting detection result to be transmitted as a position signal to the controller 1, whereby the controller 1 controls the rotation of the motor 80. That is, the controller 1 reads the position signal, and uses the read-in value to determine whether or not the first fluid supply unit 50 arrives at its coupling position (steps S3 and S4). If this determination is NO, the motor 80 is subjected to the continuous drive under the control of the controller 1.

Accordingly, the first fluid supply unit 50 is moved from the water leakage detecting nozzle 54 of the first fluid supply unit 50 to the duct coupling section 23 under a status where air is ejected.

The action of air ejecting during such a shift of the first fluid supply unit 50 removes liquid from the water leakage detecting nozzle 54 and the sleeve member surrounding the water leakage detecting nozzle 54, while reshifting liquid from an area around the water leakage detecting duct fitting 74 of the endoscope 20 located in coaxial relation to the water leakage detecting nozzle 54.

In addition, an ejecting rate of air can be varied and increasing the ejecting rate of air to be higher than that of air supplied to the Inside of the endoscope 20 for checking leaked water enables liquid drops to be further effectively removed.

The first fluid supply unit 50 is continuously moved toward the duct coupling section 23, executing initial coupling step to initiate the coupling to the duct coupling section 23. As shown in FIG. 11, more particularly, distal ends of the four guide pins 59 of the first fluid supply unit 50 begin to be slidably fitted to distal ends of the guide recesses 79 of the duct coupling section 23. Meanwhile, the packing 55p, placed on a distal end of the sleeve member 55, is brought into abutting engagement with the apical surface 23s of the duct coupling section 23, covering the outer periphery of the water leakage detecting duct fitting 74. By so doing, the water leakage detecting duct fitting 74 and the Inside of the sleeve member 55 remain closed in watertight relation.

Further, when this takes place, a distal end of the forward water supply duct 71s extending through the forward water supply duct fitting 71 of the duct coupling section 23 is inserted to the duct 51k of the forward water supply nozzle 51 of the first fluid supply unit 50. Meanwhile, a distal end of the water supply pipe 72 is inserted to the duct of the water supply nozzle 52 and a distal end of the air supply pipe 73s of the gas supply duct fitting 73 is inserted to the duct of the gas supply nozzle 53.

The first fluid supply unit 50 is further moved toward the duct coupling section 23 to the coupling position, thereby causing the first fluid supply unit 50 to be coupled completely to the duct coupling section 23.

In response to this coupling completion, the controller 1 responds to the position signal from the position sensor 84 to detect the presence of the first fluid supply unit 50 moved to the coupling position, and the controller 1 is rendered inoperative to stop the rotation of the motor 80 (step S5).

Figure 12:
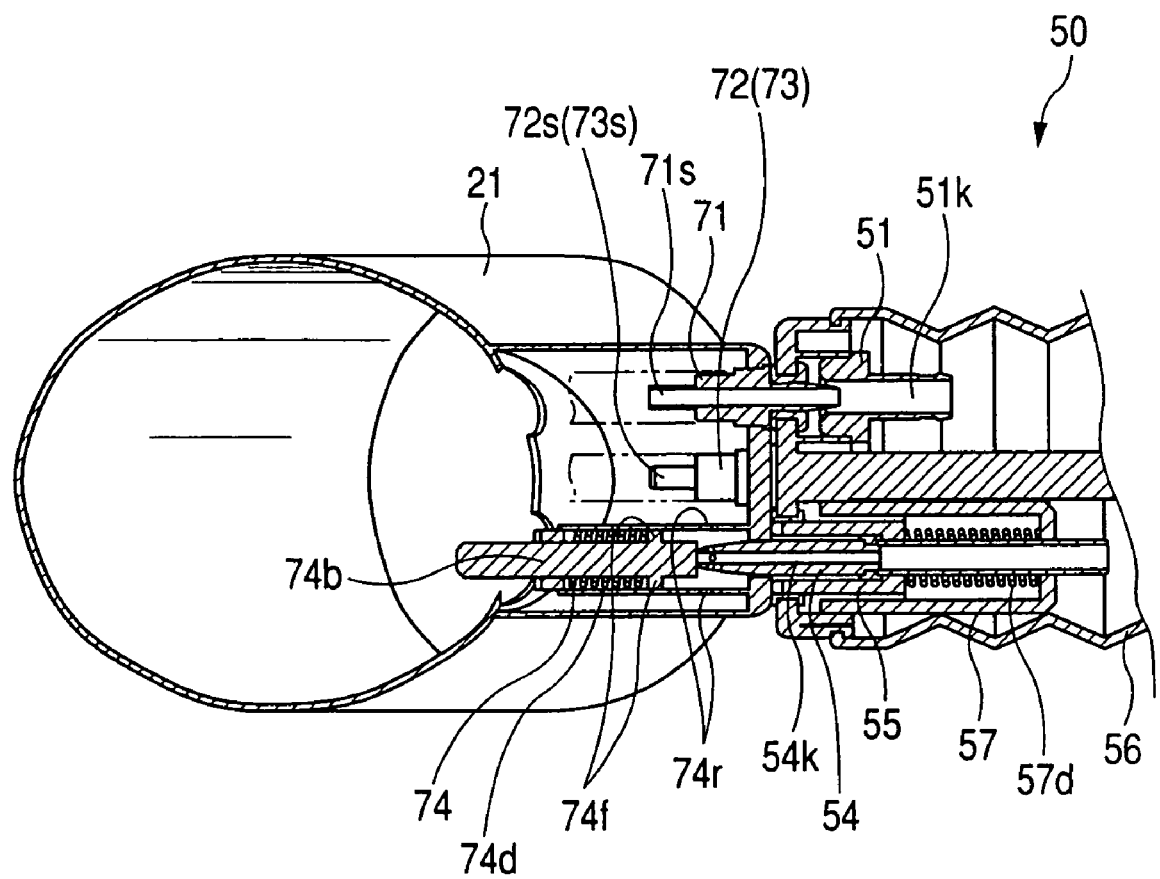
FIG. 12 is a cross sectional view showing the first fluid supply unit, the shift mechanism and the manipulator section of the endoscope for illustrating a status with the first fluid supply unit, shown in FIG. 5, being coupled to the duct coupling section.

In this coupling completed state, the four guide pins 59 of the first fluid supply unit 50 are slidably fitted to the four guide recesses 79 of the duct coupling section 23 and, as shown in FIG. 12, the duct 54k of the water leakage detecting nozzle 54 is inserted to the water leakage detecting duct fitting 74.

In addition, with the water leakage detecting nozzle 54 pressing the valve body 74b, the flange 74f is depressed toward the bottom of the water leakage detecting duct fitting 74 away from the communication aperture 74r, whereby the valve body 74b is opened. As a result, the openings, formed on the sidewall of the duct 54k at the distal end thereof, provide communication between the duct 54k and the endoscope 20.

Further, with the bottom of the sleeve member 55 depressing the spring 57d in concurrence with the valve body 74b being opened, the sleeve member 55 is inserted to the inside of the first fluid supply unit 50, that is, more particularly, to the sleeve-member support member 57.

In addition, during a phase in which the first fluid supply unit 50 is being coupled to the duct coupling section 23, the packing 55p of the sleeve member 55 remains in abutting engagement with the apical surface of the duct coupling section 23. That is, under a status where the water leakage detecting duct fitting 74 and the interior of the sleeve member 55 remain closed in watertight relation, the duct 54k of the water leakage detecting nozzle 54 is inserted in the water leakage detecting duct fitting 74 with the valve body 74b being kept in a closed state.

Thus, during inserting step, even if the first fluid supply unit 50 is coupled to the duct coupling section 23 in, for instance, liquid, no probability takes place for the water leakage detecting duct fitting 74 to cause liquid drops to penetrate into the interior of the endoscope 20.

In consecutive step S6, the controller 1 causes the leaked water detecting pump 97 to supply a given volume of air to the interior of the endoscope 20, thereby checking water leakage in the endoscope 20. More particularly, air delivered from the leaked water detecting pump 97 ejects from the openings, formed at the distal end of the duct 54k of the water leakage detecting nozzle 54, and passes through the communication apertures 74r of the water leakage detecting duct fitting 74 to the inside of the endoscope 20 for a predetermined time interval at a given pressure level.

As air is delivered at the predetermined time interval at the given pressure level, the controller 1 controls to open the relief valve 96 (see FIG. 9) (step S7) so as to interrupt the supply of air to the inside of the endoscope 20 for more than the predetermined time interval with a pressure level higher than the given pressure level. Thereafter, with the internal pressure of the duct 54k being measured with the leaked water detecting sensor 93, the operation is executed to check whether or not the water leakage area is created inside the endoscope 20 based on the measured pressure (steps S8, S9 and S10).

In next step S6, if the water leakage is not found, that is, when no water leakage area is formed in the inside of the endoscope 20, the operation goes to step S7. At this moment, the controller 1 executes operation control so as to open the exhaust valve 95 (see FIG. 9) (step S11), while causing the inside of the endoscope 20 to be released to the atmosphere via the duct 54 and the exhaust duct 78. Also, during such operation, the controller 1 may executes operation control so as to turn off the leaked water detecting pump 97 (step S12). It is not always necessary to turn off the pump 97.

In the next step S13, the controller 1 executes operation control to turn on the motor 80. At this moment, the rotary shaft 80j of the motor 80 is rotated in a reverse direction opposite to the one direction in which the first fluid supply unit 50 is moved, causing the motor gear 82 to rotate. At this moment, the motor gear 82 rotates in meshing engagement with the feed gear 83g. This causes the axial rod 83 to move protruding into the sidewall 5s in a direction perpendicular to the sidewall 5s. Meanwhile, the first fluid supply unit 50 is moved toward an area closer to the sidewall 5s in a direction perpendicular to the sidewall 5s. In this case, the controller 1 reads in the position signal and uses the read value to repeatedly determine whether or not the first fluid supply unit 50 returns and arrives at its initial position (steps S14 and S15).

In this disengagement process, the base ends of the four guide pins 59 disengages from the four guide recesses 79, respectively, and, as shown in FIG. 11, the first fluid supply unit 50 is uncoupled from the duct coupling section 23 ad retracted in the position on the initial stage for coupling.

More particularly, the distal end of the duct 54k of the water leakage detecting duct fitting 74 is uncoupled from the water leakage detecting duct fitting 74. This causes the spring 74d to protrude the valve body 74b, thereby causing the flange 74f to close the valve body 74b.

In addition, during a phase in which the first fluid supply unit 50 is moved to be uncoupled from the duct coupling section 23 to the initial coupling position, the sleeve member 55 protrudes toward the duct coupling section 23 with the packing 55p of the sleeve member 55 remains in abutting engagement with the apical surface 23s of the duct coupling section 23.

With such operation, the distal end of the duct 54k of the leaked water detecting nozzle 54 is uncoupled from the water leakage detecting duct fitting 74 thereby closing the valve body 74b with the water leakage detecting duct fitting 74 and the interior of the sleeve member 55 remaining closed in watertight relation.

Therefore, no probability takes place for the water leakage detecting duct fitting 74 to cause liquid drops to penetrate into the inside of the endoscope 20 even if the first fluid supply unit 50 is uncoupled from the duct coupling section 23 in liquid.

More particularly, after the detection of leaked water, disinfecting step is executed to disinfect the forward water supply duct fitting 71, the water supply duct fitting 72 and the gas supply duct fitting 73. Therefore, even if the first fluid supply unit 50 is uncoupled from the duct coupling section 23, no liquid drop is caused to penetrate into the interior of the endoscope 20 from the water leakage detecting duct fitting 74 and the apical surface 23s and the forward water supply duct fitting 71, the water supply duct fitting 72 and the gas supply duct fitting 73 can be immersed in disinfecting liquid.

After the first fluid supply unit 50 has been uncoupled from the duct coupling section 23 and moved to the initial coupling position, the controller 1 commands the motor 80 to stop its rotation (step S16).

Afterward, the forward water supply nozzle 51 of the first fluid supply unit 50 supplies disinfecting or washing water to the forward water supply duct fitting 71 of the duct coupling section 23. Meanwhile, the water supply nozzle 52 supplies disinfecting or washing water to the water supply duct fitting 72 and the gas supply nozzle 53 supplies disinfecting or washing water to the gas supply duct fitting 73. In such a way, washing and disinfecting steps are carried out. In addition, various steps subsequent to such steps are well known in the art and, hence, detailed description of the same is herein omitted.

Meanwhile the controller 1 returns its processing to step S10, in which if the leaked water checking result is found to be negative, that is, when the leaked water area is formed in the interior of the endoscope 20, then, the operation is branched off to step S17. In step S17, the controller 1 executes operation control so as to allow, for instance, an operation panel (see FIG. 1) to provide an alarm display for the possibility of a water leakage from the endoscope 20.

Thereafter, the exhaust valve 95 (see FIG. 9) is opened (step S11), causing the interior of the endoscope 20 to be released to the atmosphere via the duct 54k and the exhaust valve 95. And the step S12 and successive steps are repeated by the controller 1 in the same way as the foregoing, whereby the first fluid supply unit 50 is moved to an uncoupling position, shown in FIG. 8, to be uncoupled from the duct coupling section 23.

That is, the four guide pins 59 slide and disengage from the four guide recesses 79, causing the nozzles 51 to 54 to be uncoupled from the fittings 71 to 74, respectively. In addition, the packing 55p of the sleeve member 55 protrudes toward the coupling section 23 due to the spring force of the spring 57d so as to cover the outer periphery of the water leakage detecting nozzle 54.

Subsequently, the top cover 4 is opened by the operator and the tray 10 is removed after which the endoscope 20 is taken out of the tray 10 for repair thereof.

Thus, the first embodiment of the present invention has been described with reference to a structure wherein the forward water supply duct fitting 71, the water supply duct fitting 72, the gas supply duct fitting 73 and the water leakage detecting duct fitting 74 are provided on the duct coupling section 23 of the manipulator section 21 forming the endoscope 20 with respective end faces disposed in parallel to the apical surface 23s.

Further, the first embodiment has been described in connection to a structure wherein with the first fluid supply unit 50, the forward water supply nozzle 51, the water supply nozzle 52, the gas supply nozzle 53 and the leaked water detecting nozzle 54 are oriented in the same connecting direction.

Furthermore, the first embodiment has been described in conjunction with a structure wherein: the forward water supply nozzle 51 is disposed in coaxial relation to the forward water supply duct fitting 71; the water supply nozzle 52 is disposed in coaxial relation to the water supply duct fitting 72; the gas supply nozzle 53 is disposed in coaxial relation to the gas supply duct fitting 73; and the leaked water detecting nozzle 54 is disposed in coaxial relation to the water leakage detecting duct fitting 74.

Moreover, the first fluid supply unit 50 has been described with reference to an example that includes a single motor 80 operative to move to the coupling initial position, the coupling position and the uncoupling position. In addition, the first fluid supply unit 50 has been described in conjunction with a structure that can be moved from the uncoupling position to the coupling position with the leaked water detecting nozzle 54 remaining in an operative state for ejecting air.

With such an arrangement, the use of only the single motor automatically allows the first fluid supply unit 50 to easily perform operation control for achieving the coupling and uncoupling operations. This results in capability of achieving a reduction in time needed for washing and disinfecting steps.

In addition, with the leaked water detecting nozzle 54 arranged to eject air during the operation in which with the leaked water detecting nozzle 54 is automatically inserted to the water leakage detecting duct fitting 74, an air stream is effective to remove liquid adhered onto an area in a space between the leaked water detecting nozzle 54 and the sleeve member covering the outer periphery of the leaked water detecting nozzle 54. Moreover, the air stream removes liquid adhered onto the neighborhood of the water leakage detecting duct fitting 74 of the duct coupling section 23 of the endoscope 20 located in face-to-face relationship with the leaked water detecting nozzle 54. Therefore, during the uncoupling operation, no liquid can flow from the water leakage detecting duct fitting 74 into the interior of the endoscope in a reliable fashion.

Further, during a phase in which the leaked water detecting nozzle 54 is coupled to or uncoupled from the water leakage detecting duct fitting 74, the valve body 74b is closed or opened with the sleeve member 55 keeping the water leakage detecting duct fitting 74 and the inside of the sleeve member 55 in watertight relation. Thus, during the coupling and uncoupling operations, liquid can be reliably prevented from entering into the inside of the endoscope from the water leakage detecting duct fitting 74.

Also, a modified form will be described below. While the present embodiment has been described with reference to an example wherein during the operations to clean and disinfect the therapeutic-tool insertion duct, the therapeutic-tool insertion duct fitting 24a is connected to the therapeutic-tool insertion duct supply nozzle 61, located at the distal end of the second fluid supply unit 60, through, for instance, the tube, the present invention is not limited to such an arrangement. It is, of course, to be appreciated that the second fluid supply unit 60 may be moved in the same manner as the first fluid supply unit 50 to allow the therapeutic-tool insertion duct supply nozzle 61 to be automatically inserted to the therapeutic-tool insertion duct fitting 24a.

Second Embodiment

A second embodiment is described with reference to FIGS. 13 to 22.

A washing and disinfecting apparatus of the present embodiment differs from the washing and disinfecting apparatus of the first embodiment in respect of structures of the first fluid supply unit and the associated shift mechanism under circumstances where the duct coupling section of the manipulator section of the endoscope accommodated in the washing and disinfecting apparatus includes the forward water supply duct fitting, the water supply duct fitting and the air fed duct fitting placed on the same plane in one row. Therefore, the present embodiment is described below with a focus on such a differing point with the same component parts as those of the first embodiment bearing like reference numerals to omit redundant description.

Figure 13:
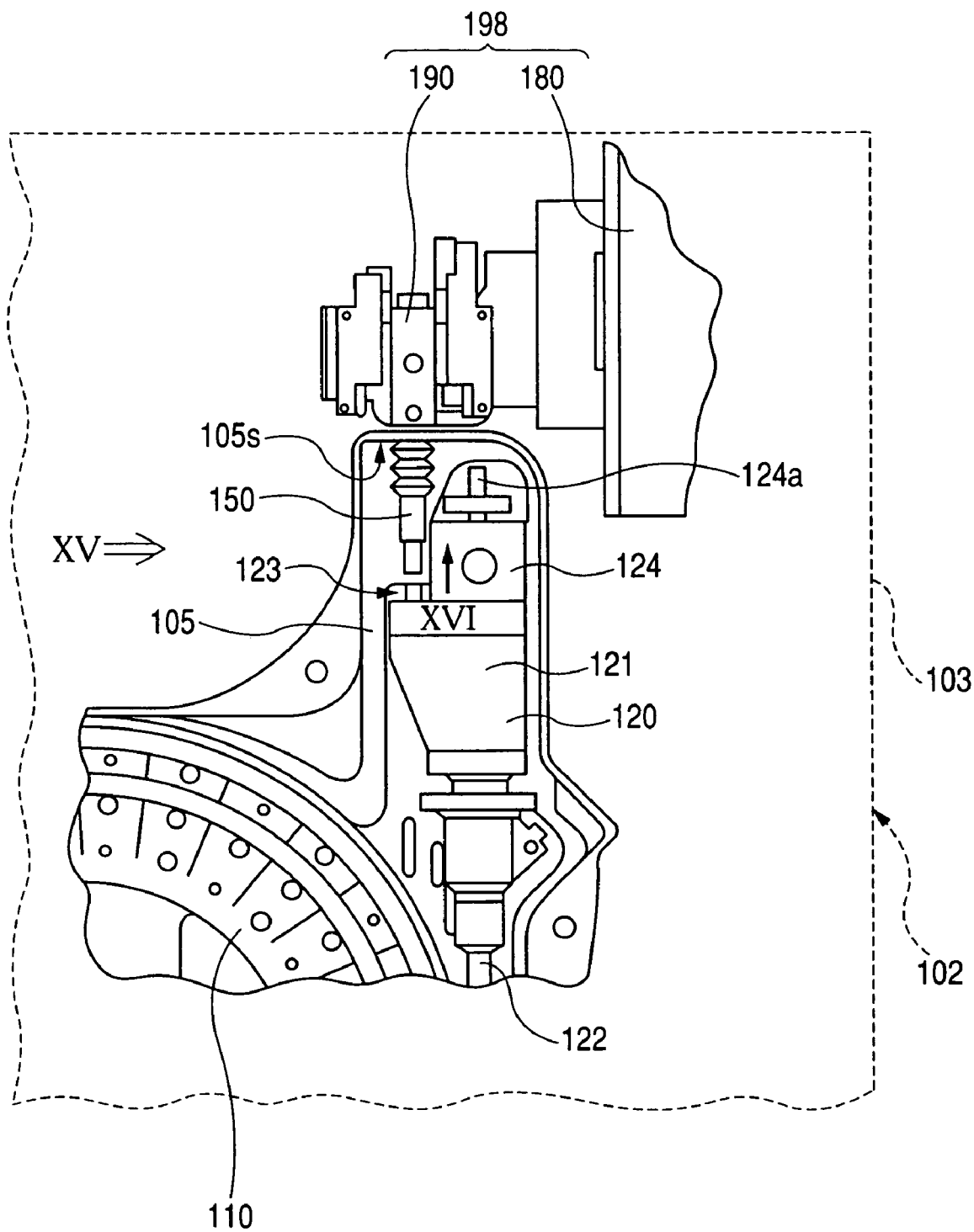
FIG. 13 is a plan view showing a part of a structure of an endoscope washing and disinfecting apparatus of a first embodiment according to the present invention together with a tray and a manipulator of an endoscope.

As shown in FIG. 13, an endoscope washing and disinfecting apparatus 102 has an apparatus body 103 that has an upper area formed with a washing and disinfecting bath 105 with a given depth which has an endoscope accommodating opening, opening upward, which is adapted to be opened or closed with a top cover 4. In addition, the washing and disinfecting bath 105 is available to receive a tray 110 on which an endoscope 120 is accommodated.

The endoscope 120, accommodated in or removed from the tray 110, comprises a major section that includes a manipulator section 121 and a flexible inserting section 122 extending from the manipulator section 121. The manipulator section 121 has a base end having a surface from which a duct coupling section 123 and a therapeutic-tool coupling section 124 stands upright at areas spaced from each other.

Figure 15:
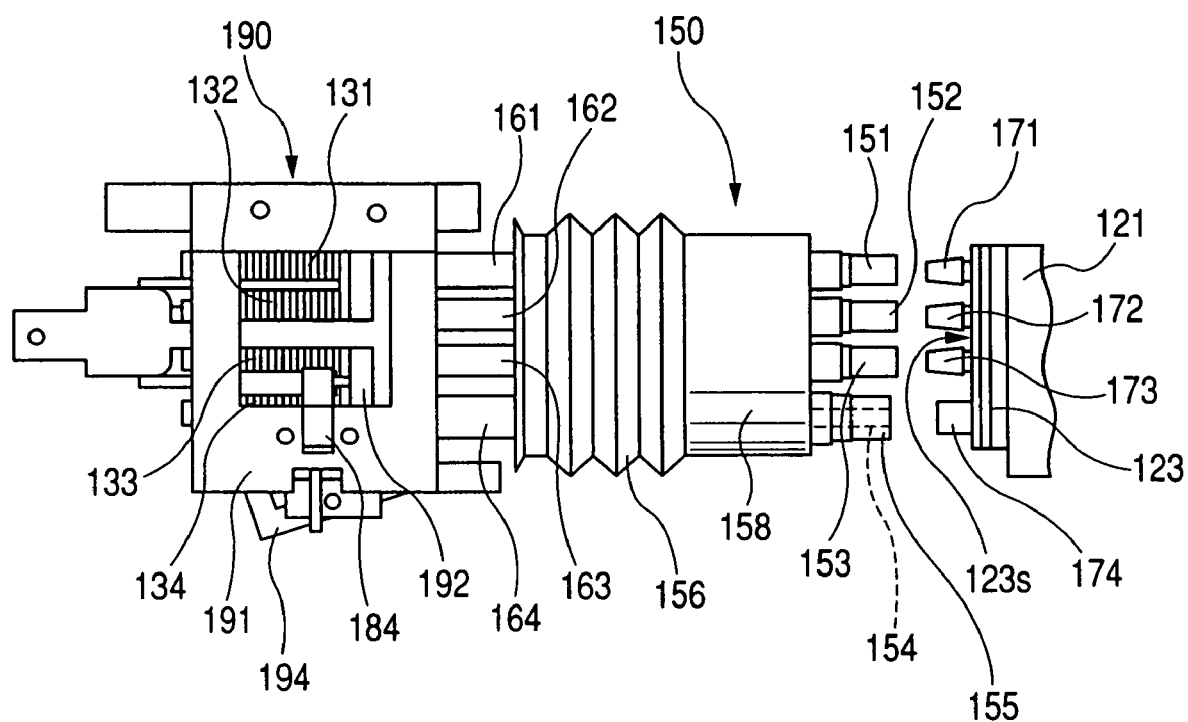
FIG. 15 is a side view showing only the first fluid supply unit, shown in FIG. 13, as viewed in a direction XV.

As shown in FIG. 15, the duct coupling section 123 has an apical surface 123s carrying thereon a forward water supply duct fitting 171, playing a role as a fluid duct fitting having an opening exposed to the manipulator 121 of the forward water supply duct disposed inside the manipulator section 121 and the inserting section 122, a water supply duct fitting 172, playing a role as a fluid duct fitting having an opening exposed to the manipulator section 121, and an gas supply duct fitting 173 playing a role as a fluid duct fitting having an opening exposed to the manipulator section, with these component parts standing upright from the apical surface 123s.

Further, a water leakage detecting duct fitting 174 is provided on the apical surface 123s so as to protrude therefrom and has an opening communicating with an interior of the endoscope 120. Also, the water leakage detecting duct fitting 174 has an end face closer to the apical surface 123s than end faces of the respective duct fittings 171 to 173.

The water leakage detecting duct fitting 174, formed in a bottomed wall though not shown, receives therein a coil spring 174d to which a valve body 174b, formed with a flange 174f, is inserted as shown in FIG. 7. In addition, the flange 174f is fitted to the coil spring 174d. Moreover, the water leakage detecting duct fitting 174 has a peripheral wall formed with communication apertures 174r communicating with the inside of the endoscope 120.

The valve body 174b normally remains closed with the flange 174f assuming a position closer to the apical surface 123s than the communication apertures 174r. Meanwhile, the valve body 174b is opened only when a water leakage detecting nozzle 154, described later, is inserted to the water leakage detecting duct fitting 174 and the flange 174f of the valve body 174b is pressed against the bottomed wall of the water leakage detecting duct fitting 174 away from the communication apertures 174r.

Further, the forward water supply duct fitting 171, the water supply duct fitting 172, the gas supply duct fitting 173 and the water leakage detecting duct fitting 174 stand upright from the apical surface 123s in parallel to each other.

Furthermore, the respective duct fittings 171 to 174 have the same functions as the respective duct fittings 71 to 74 of the first embodiment set forth above and, hence, redundant description of the same is herein omitted.

The therapeutic-tool coupling section 124 has a distal end provided with a therapeutic-tool insertion duct fitting 124a having an opening connected to the manipulator section 121 of a therapeutic-tool inserting pipe disposed inside the manipulator section 121 and the inserting section 122. For the therapeutic-tool inserting pipe to be washed and disinfected, the therapeutic-tool insertion duct fitting 124a is connected to the therapeutic-tool inserting pipe supply nozzle 61 (see FIG. 1), provided on the distal end of the second fluid supply unit 60 described with reference to the first embodiment mentioned above, via for instance a tube or the like. In addition, like the first embodiment, an alternative may take the form of a structure arranged to automatically insert the therapeutic-tool inserting pipe supply nozzle 61 to the duct fitting 124a.

The tray 110 defines a position of the duct coupling section 123 to be placed in face-to-face relation to the first fluid supply unit 150, described below, That is, the tray 110 constitutes a position defining means in the present invention.

A shift mechanism 198, described below, is drivably connected to and move the fluid duct fluid supply unit (hereinafter referred to as a first fluid supply unit) 150 to be closer to and away from (in a protruding state) a sidewall 105s of the washing and disinfecting bath 105 in a direction perpendicular thereto.

Figure 14:
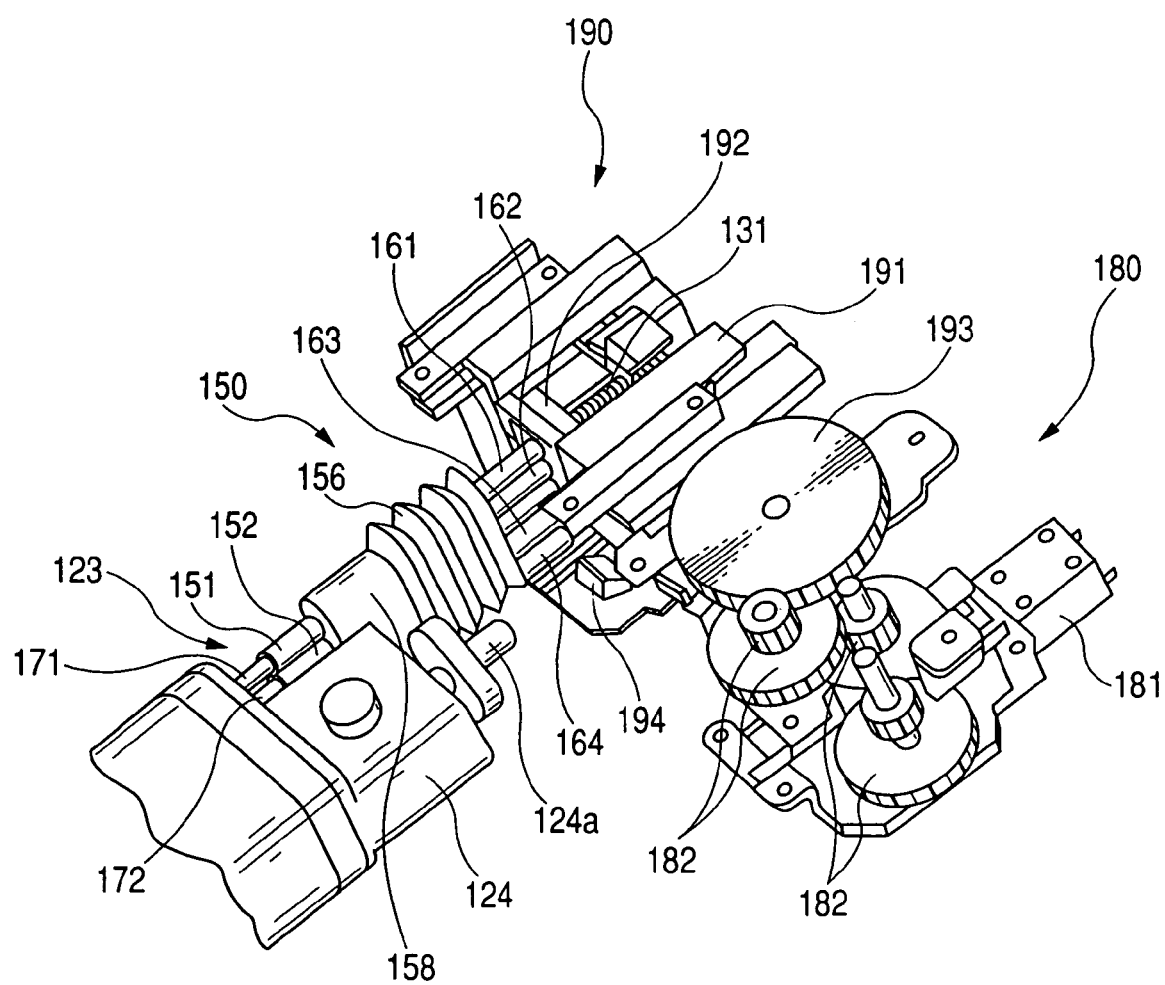
FIG. 14 is a perspective view showing a first fluid supply unit, shown in FIG. 13, together with a shift mechanism of the unit and a duct coupling section of an endoscope manipulator.

As shown in FIGS. 13 to 15, the first fluid supply unit 150 has a major structure that includes pipe-like members 161 to 164, extending through the sidewall 105s in a direction perpendicular thereto and protruding into the washing and disinfecting bath 105, a distal end portion 158 through which the pipe-like members 161 to 164 extend and are fixedly supported, and a tube-shaped accordion-like member 156, made of for instance rubber with a square shape in cross section, which has one end connected to the distal end portion 158 and covering outer peripheries of the pipe-like members 161 to 164 at areas protruding from the sidewall 105s.

Figure 17:
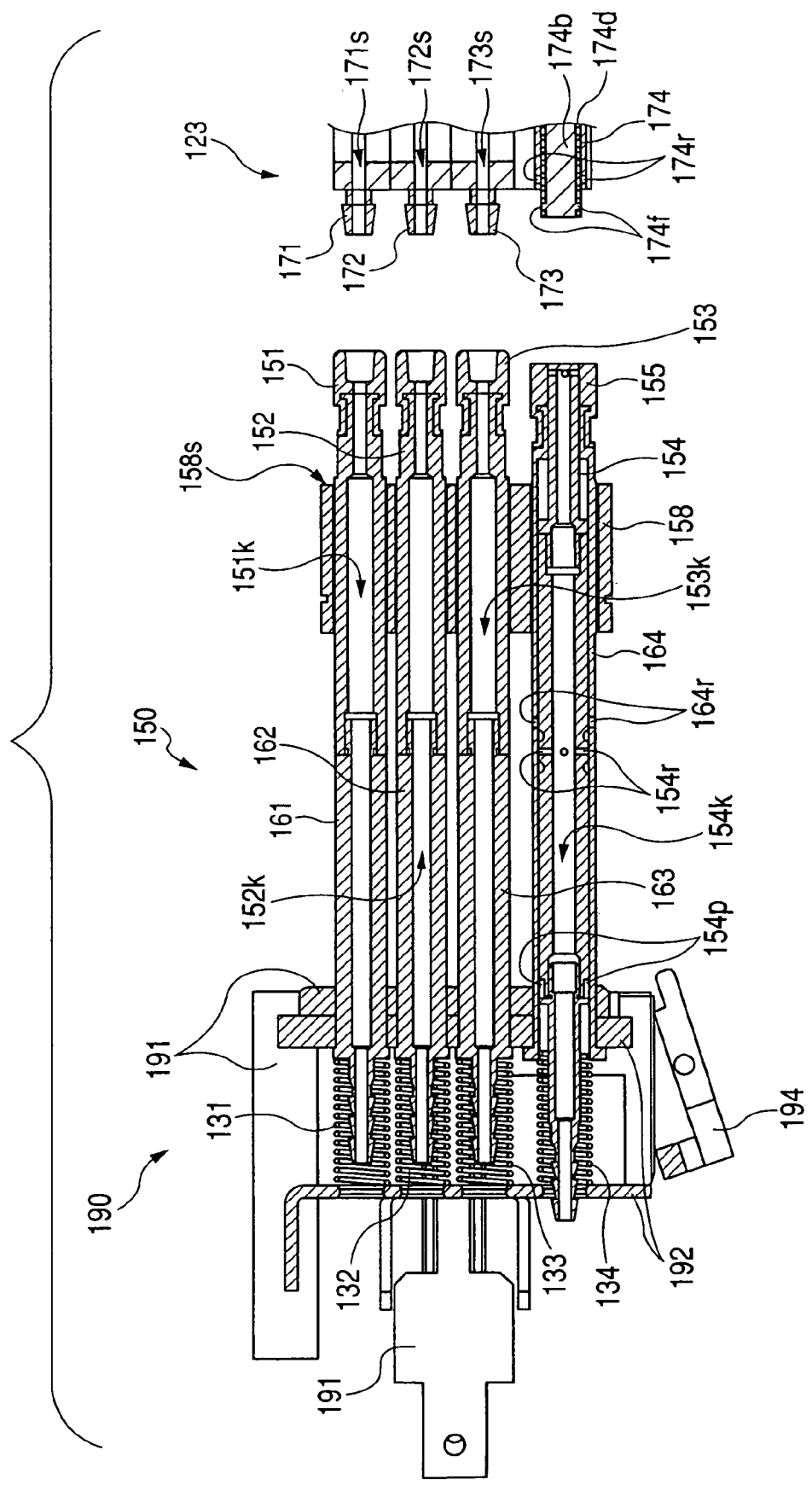
FIG. 17 is a cross sectional view taken on line XVII-XVII of FIG. 16.

In addition, the pipe-like members 161 to 164 are arranged in one row in parallel to each other on the same plane. Moreover, as shown in FIG. 17, the pipe-like member 164 has a wall surface formed with communication apertures 164r at given positions.

Further, the pipe-like member 164 is formed with a shift aperture 164h (see FIG. 8) to which a part of a shift member 191 is fitted for shifting a water leakage detecting nozzle 154, described below, to a coupling (inserting) position.

As shown in FIG. 13, further, the first fluid supply unit 150 is fixedly mounted on the sidewall 105s of the washing and disinfecting bath 105 so as to protrude therefrom in a direction perpendicular to the sidewall 105s. More particularly, a support unit 190, forming part of the shift mechanism 198, is provided on a rear side of the sidewall 105s for fixedly supporting the first fluid supply unit 150.

As shown in FIGS. 14 and 15, the support unit 190 has a major structure that comprises fixing members 192, a shift member 191, a claw portion 194 provided on the fixing member 192, a position sensor 184 provided on the shift member 191, and a rack gear 193.

The fixing members 192 have base ends having bottom walls, which support base ends of the pipe-like members 161 to 164 by means of coil springs 131 to 134, respectively, and four insertion holes to which the respective pipe-like members are inserted.

The shift member 191 is formed with four holes through which the pipe-like members 161 to 164 extend. The shift member 191 is associated with the rack gear 193 to be movable with the respective pipe-like members 161 to 164 to a coupling position to be closer to the duct coupling section 123 and an uncoupling position to a way from the duct coupling section 123. Also, the claw portion 194 serves to fixedly retain the shift member 191 in an initial coupling position.

Further, the shift member 191 is formed with a shift pin 191p (see FIG. 8), which with the claw portion 194 held in engagement with the fixing members 192, is held in fitting engagement with the shift aperture 164h of the pipe-like member 164 for shifting only the water leakage detecting nozzle 154 in the pipe-like member 164 toward the duct coupling section 123.

Further, the position sensor 184 serves to detect a position of the shift member 191, that is, a position of the first fluid supply unit 150 and transmits the relevant detection result to the controller 1 (see FIG. 9).

The rack gear 193, playing a role as a gear held in abutting engagement with a sidewall of the shift member 191 for rotating capability, is rotated by a drive unit 180 to move the shift member 191 to a coupling position, an initial coupling position and an uncoupling position.

Furthermore, the drive unit 180, forming a part of the shift mechanism 198, is provided on a reverse side of the sidewall 105s for driving the support unit 190. The drive unit 180 comprises a motor 181, and a reduction gear train 182 including a plurality of pinion gears held in meshing engagement with each other. With the motor 181 turned on to rotate, the reduction gear train 182 is caused to rotate, thereby rotating the rack gear 193, held in meshing engagement with the reduction gear train 182, at a reduced speed.

With the motor 181 energized to rotate in one direction, an output torque of the motor 181 is transferred through the reduction gear train 182 to the rack gear 193, meshing therewith, which is consequently caused to rotate in one direction at the reduced speed. This output torque is transferred from the rack gear 193 to a sidewall of the shift member 191, which is consequently moved from the uncoupling position to the coupling position at a low speed.

Further, with the motor 181 energized to rotate in another direction opposite to the one direction, the output torque of the motor 181 is transferred through the reduction gear train 182 to the rack gear 193, meshing therewith, which is consequently caused to rotate in another direction opposite to the one direction at a reduced speed. This output torque is transferred from the rack gear 193 to the sidewall of the shift member 191, which is consequently moved from the coupling position to the uncoupling position at a low speed.

Figure 16:
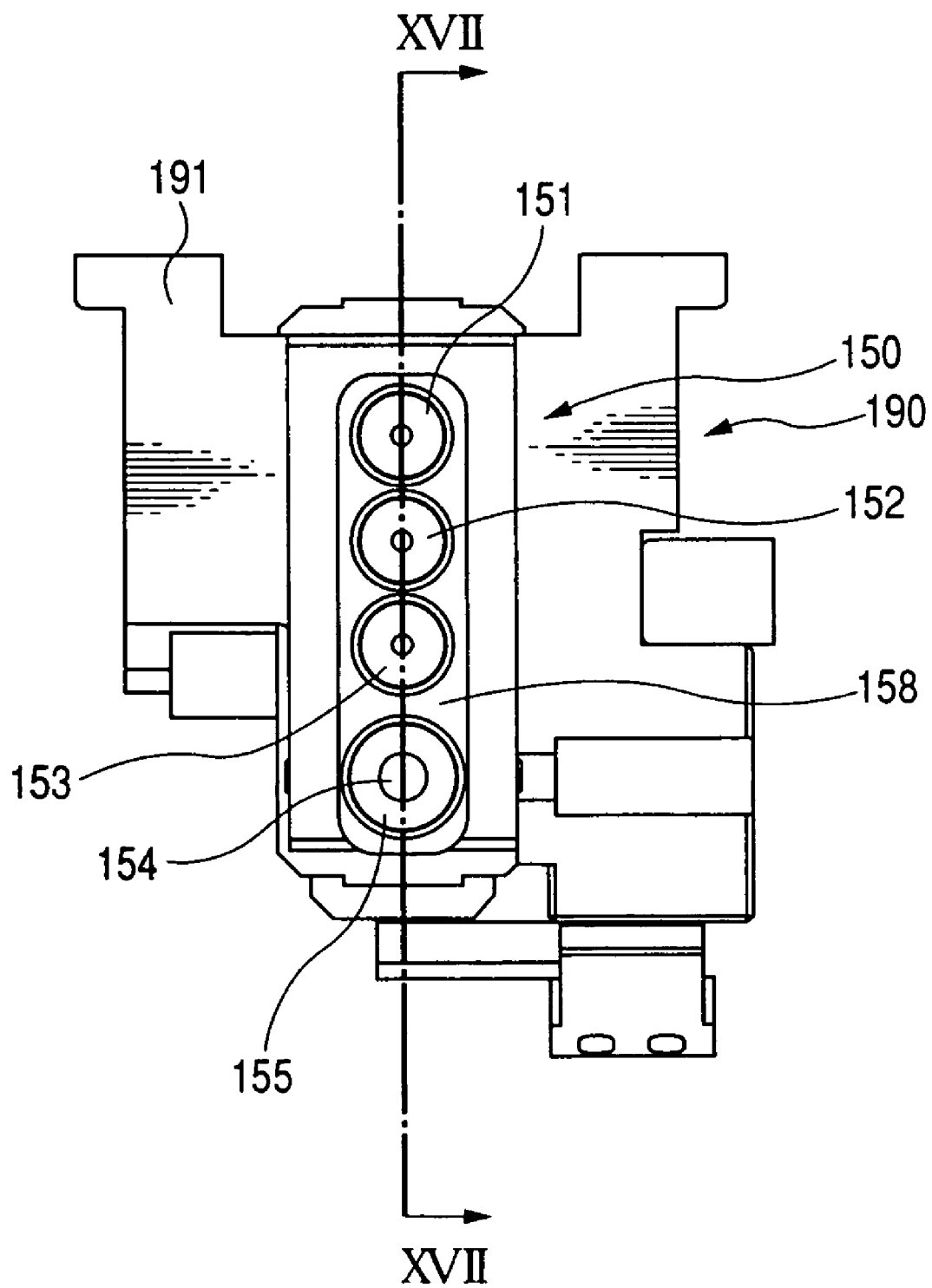
FIG. 16 is a front view showing a shape of a distal end of the first fluid supply unit, shown in FIG. 13, as viewed I a direction XVI.

As shown in FIGS. 15 to 17, the pipe-like member 161 has a forward water supply nozzle 151, appearing at a distal end of the distal end portion 158 and playing a role as a fluid supply nozzle, and the pipe-like member 162 has a water supply nozzle 152, appearing at the distal end of the distal end portion 158 and playing a role as a fluid supply nozzle. In addition, the pipe-like member 163 has an gas supply nozzle 153, appearing at the distal end of the distal end portion 158 and playing a role as a fluid supply nozzle, and the pipe-like member 164 has the water leakage detecting nozzle 154.

Further, the forward water supply nozzle 151 is located in coaxial relation to the forward water supply duct fitting 171 and the water supply nozzle 152 is located in coaxial relation to the water supply duct fitting 172. In addition, the gas supply nozzle 153 is located in coaxial relation to the gas supply duct fitting 173 and the water leakage detecting nozzle 154 is located in coaxial relation to the water leakage detecting duct fitting 174. This results in a consequence with these nozzles being placed on the same plane in one raw as shown in FIG. 16.

The forward water supply nozzle 151 is connected to an outer periphery of a duct 151k, as shown in FIG. 17, at an area, protruding from an apical surface 158s, which extends from the pipe-like member 161 branched off from the common duct 90 (see FIG. 9) having its one end, connected to the stirring bath 32 as described below, and a distal end to which the duct 151k is opened.

The water supply nozzle 152 is connected to an outer periphery of a duct 152k, as shown in FIG. 17, at an area, protruding from the apical surface 158s, which extends from the pipe-like member 162 branched off from the common duct 90 (see FIG. 9) having its one end, connected to the stirring bath 32 as described below, and a distal end to which the duct 152k is opened.

The gas supply nozzle 153 is connected to an outer periphery of a duct 153k, as shown in FIG. 17, at an area, protruding from the apical surface 158s, which extends from the pipe-like member 163 branched off from the common duct 90 (see FIG. 9) having its one end, connected to the stirring bath 32 as described below, and a distal end to which the duct 152k is opened.

The water leakage detecting nozzle 154 is connected to an outer periphery of the other end of a duct 154k, as shown in FIG. 17, at an area protruding from the apical surface 158s, which has one end connected to the leaked water detecting pump 97 (see FIG. 9) and allows a distal end and a sidewall at which the duct 154k is opened.

Further, the water leakage detecting nozzle 154 is formed with communication apertures 154r at given positions for relief functions. With the water leakage detecting nozzle 154 shifted to a relief position described below, the communication apertures 154r are brought into alignment with the communication apertures 164r, thereby permitting air in the duct 154k to be exhausted to the outside. In addition, the water leakage detecting nozzle 154 has a base end portion formed with pin recesses 154p to which the shift pin 191p is held in fitting engagement.

Furthermore, a sleeve member 155 is disposed on an outer periphery of the water leakage detecting nozzle 154 at an area protruding from the apical surface 158s of the distal end portion 158 in coaxial relation to the water leakage detecting nozzle 154 and covers the outer periphery of the water leakage detecting nozzle 154.

Moreover, with the first fluid supply unit 150 coupled to the duct coupling section 123, the sleeve member 155 is brought into abutting engagement with an apical surface of the water leakage detecting duct fitting 174 and covers the outer periphery of the water leakage detecting duct fitting 174, thereby closing the water leakage detecting duct fitting 174 and the sleeve member 155 in watertight relation.

In addition, the endoscope washing and disinfecting apparatus 102 has the same structure in other respect as the structure of the endoscope washing and disinfecting apparatus 102 of the first embodiment set forth above and, hence, description of the same is herein omitted.

Next, the operation of the endoscope washing and disinfecting apparatus 102 is described below with reference to FIGS. 13 to 17 and FIGS. 18 to 22.

Also, the operation of the endoscope washing and disinfecting apparatus 102 is described with a focus on only leaked water detecting step for checking whether or not a leaked water area is created in the Inside of the endoscope 120.

Next, for the first fluid supply unit 150 to be coupled to the duct coupling section 123, the controller 1 (see FIG. 9) executes operation control so as to turn on the leaked water detecting pump 97 (see FIG. 9). This allows the leaked water detecting pump 97 to supply air to the duct 154k, thereby causing air to be ejected from the water leakage detecting nozzle 154 connected to the distal end of the duct 154k.

Then, the controller 1 (see FIG. 9) executes operation control so as to turn on the motor 181. This allows the reduction gear train 182 to rotate, causing the rack gear 193 held in meshing engagement with the reduction gear train 182 to rotate in one direction at a reduced speed. This allows the shift member 191 to be moved toward the duct coupling section 123 at a low speed.

Further, the first fluid supply unit 150 is moved from the water leakage detecting nozzle 154 toward the duct coupling section 123 with air remaining in an injecting state.

The presence of air injecting during such a shift of the first fluid supply unit 150 removes liquid from between the water leakage detecting nozzle 154 and the sleeve member 155 covering the outer periphery of the water leakage detecting nozzle 154, while reshifting liquid adhered onto the neighboring of the water leakage detecting duct fitting 174 forming the duct coupling section 123 located in face-to-face relation to of the water leakage detecting nozzle 154.

In addition, an ejecting rate of air can be varied and it is advisable to regulate the ejecting rate of air such that the greater the volume of air than the volume of air to be supplied into the interior of the endoscope 120 for checking water leakage, the more effective for liquid droplets to be removed.

Figure 18:
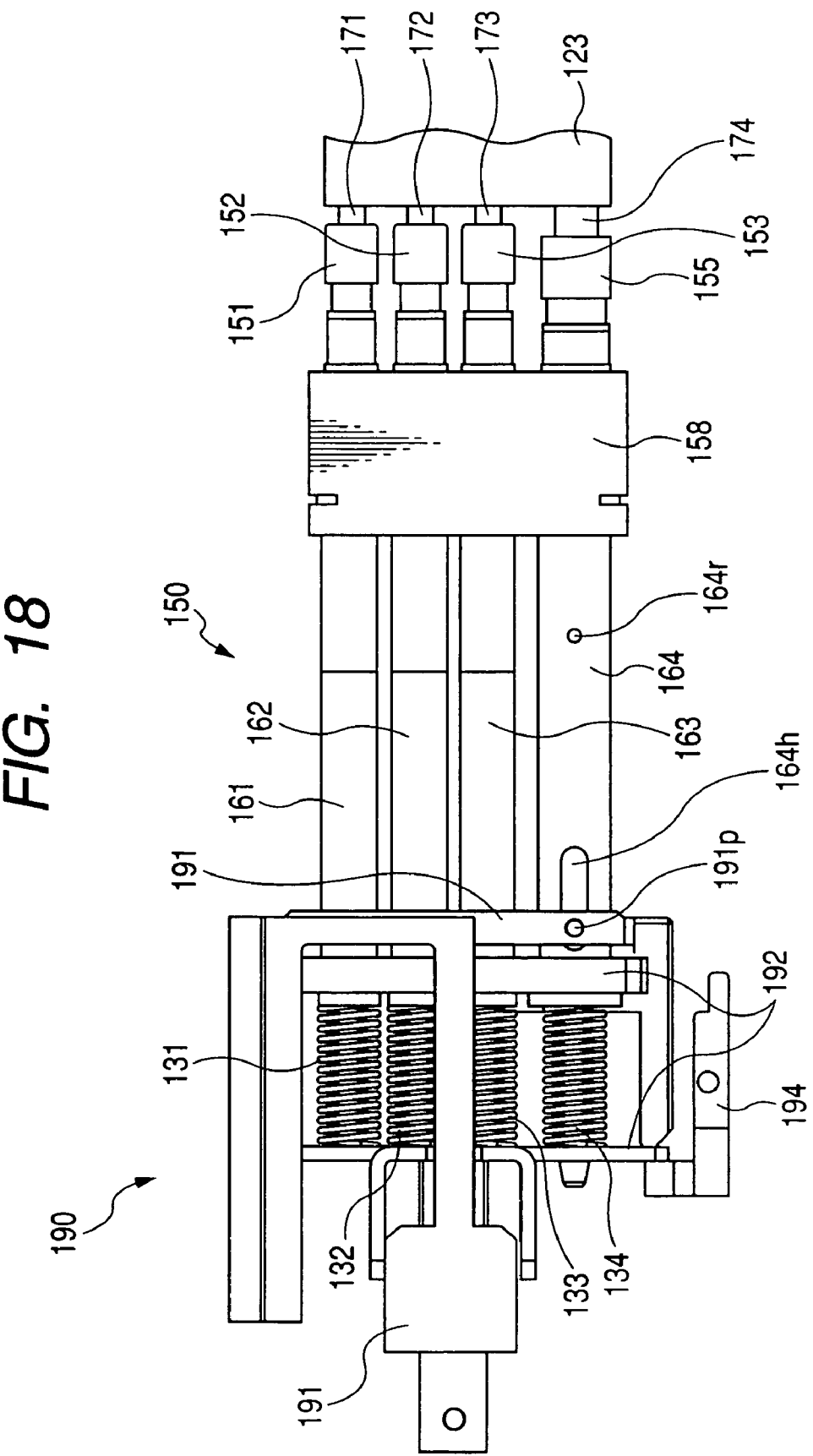
FIG. 18 is a plan view showing the first fluid supply unit, a support unit and the duct coupling section for illustrating an initial status wherein the first fluid supply unit, shown in FIG. 13, is coupled to the duct coupling section.
Figure 19:
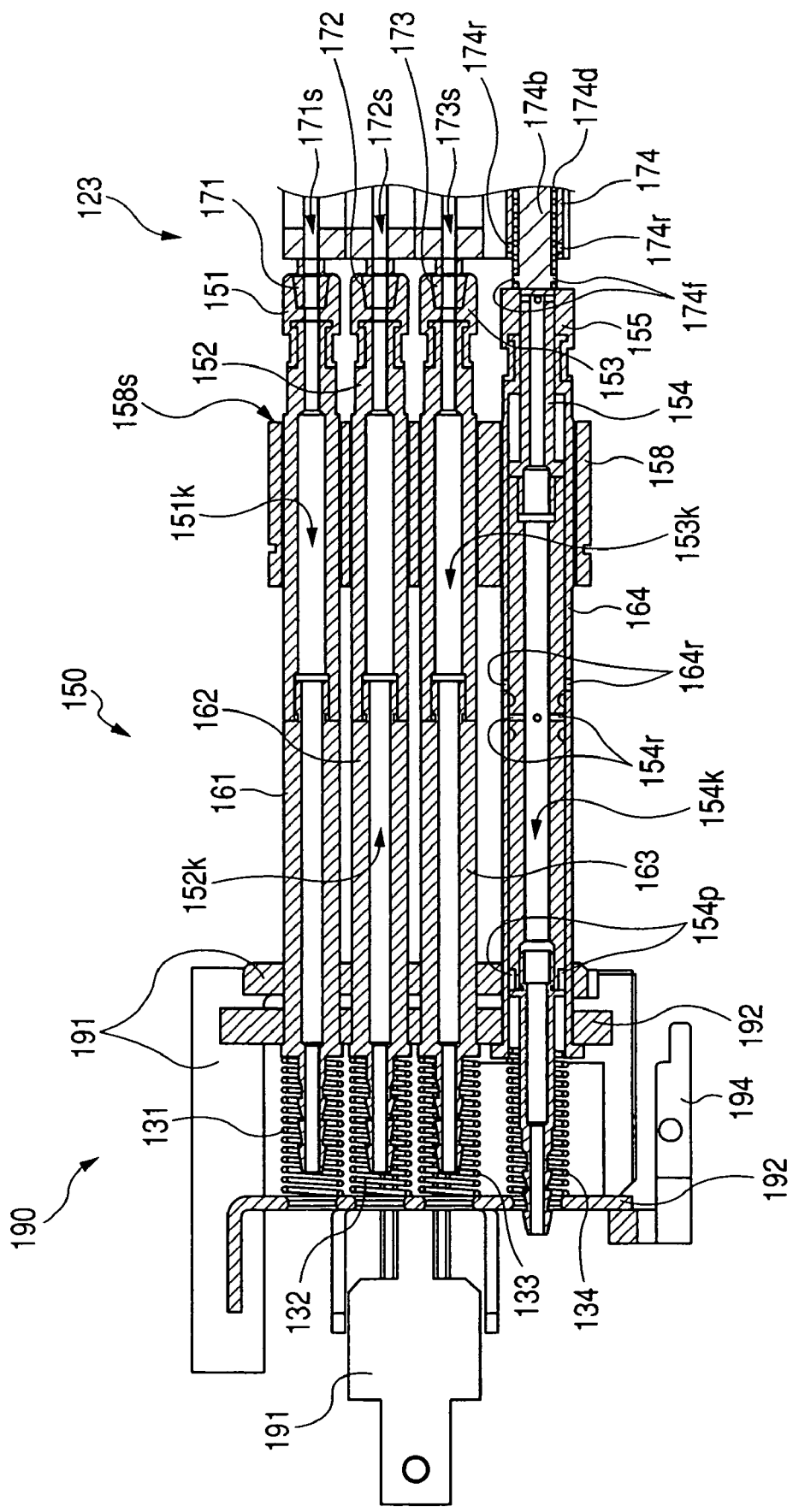
FIG. 19 is a cross sectional view showing the first fluid supply unit, shown in FIG. 18, the support unit and the duct coupling section.

Next, due to the movement of the first fluid unit 150 toward the duct coupling section 123 to the initial coupling position, as shown in FIGS. 18 and 19, the distal end of the sleeve member 155 is brought into abutting engagement with an apical surface of the water leakage detecting duct fitting 174. This allows the water leakage detecting duct fitting 174 and the interior of the sleeve member 155 to be closed in watertight relation.

When this takes place, further, a distal end of a forward water supply duct 171s of the forward water supply duct fitting 171 of the duct coupling section 123 is inserted to the duct 151k of the forward water supply nozzle 151 of the first fluid supply unit 150. A distal end of a water supply pipe 172s of the water supply duct fitting 172 is inserted to the duct 152k of the water supply nozzle 152. A distal end of an air supply pipe 173s of the gas supply duct fitting 173 is inserted to the duct 153k of the gas supply nozzle 153. In addition, as shown in FIG. 18, the claw portion 194 is brought into clamping engagement with the base end of the fixing member 192.

Then, under a status where the shift pin 191p of the shift member 191 is fitted to the pin recess 154p of the water leakage detecting nozzle 154 via the shift aperture 164h of the pipe-like member 164, shifting the first fluid supply unit 150 further toward the duct coupling section 123 to the coupling position allows the first fluid supply unit 150 to be coupled to the duct coupling section 123.

Moreover, the position sensor 184 detects whether or not the first fluid supply unit 150 is moved to the coupling position. That is, when the position sensor 184 detects that the first fluid supply unit 150 is moved to the coupling position, the controller 1 stops the rotation of the motor 181.

Figure 20:
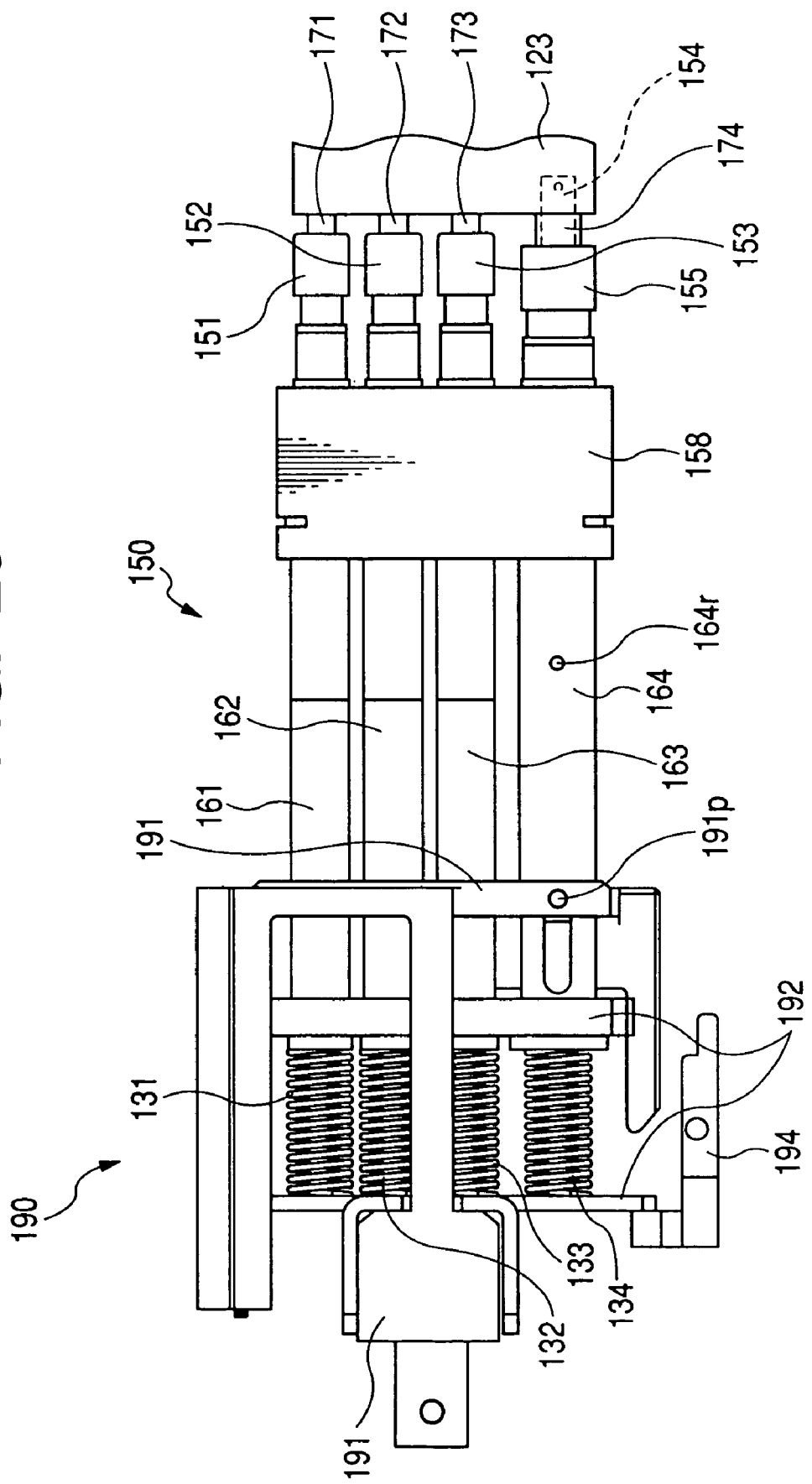
FIG. 20 is a plan view showing the first fluid supply unit, the support unit and the duct coupling section for illustrating a status wherein the first fluid supply unit, shown in FIG. 13, is coupled to the duct coupling section.
Figure 21:
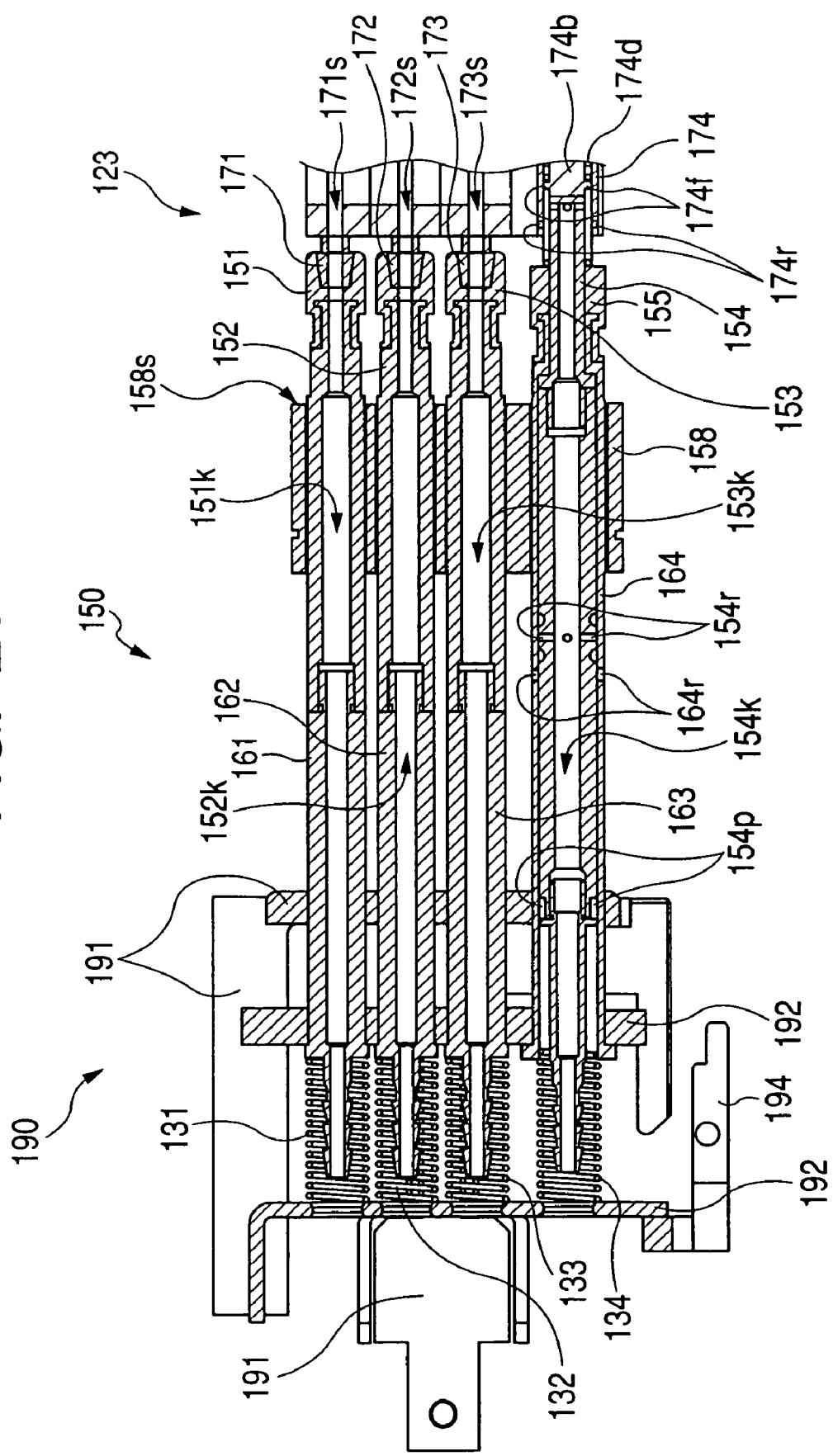
FIG. 21 is a cross sectional view showing the first fluid supply unit, shown in FIG. 20, the support unit and the duct coupling section.

More particularly, due to the presence of the water leakage detecting nozzle 154 placed in coaxial relation to the water leakage detecting duct fitting 174, only the water leakage detecting nozzle 154 is inserted to the inside of the water leakage detecting duct fitting 174 due to sliding engagement between the shift pin 191p of the shift member 191 and the pin recess 154p as shown in FIGS. 20 and 21.

Thereafter, the water leakage detecting nozzle 154 depresses the valve body 174b, thereby pressing the flange 174f toward the bottom wall of the water leakage detecting duct fitting 174 away from the communication apertures 174r. This results in communication between the duct 54k and the inside of the endoscope 120 via the openings formed on the sidewall of the duct 54k.

Moreover, during the movement in which the first fluid supply unit 150 is coupled to the duct coupling section 123, the sleeve member 155 remains operative to be held in abutting engagement with the distal end of the water leakage detecting duct fitting 174 of the duct coupling section 123. That is, under a status where the water leakage detecting duct fitting 174 and the interior of the sleeve member 155 remains tightly closed in watertight relation, the water leakage detecting nozzle 154 is inserted to the water leakage detecting duct fitting 174 with the valve body 174b remaining in a closed state.

For the reason mentioned above, no probability takes place for liquid droplets to penetrate from the water leakage detecting duct fitting 174 into the interior of the endoscope 120 even under a status where the first fluid supply unit 150 is coupled to the duct coupling section 123 in liquid.

Then, the leaked water detecting pump 97 supplied air to the interior of the endoscope 120 at a given rate, thereby executing the checking of water leakage occurring in the interior of the endoscope 120. More particularly, an air stream, delivered from the leaked water detecting pump 97, is supplied through the openings formed on the sidewall of the duct 54k of the water leakage detecting nozzle 154 and the communication apertures 174r of the water leakage detecting duct fitting 174 into the interior of the endoscope 120 for a predetermined time interval until a pressure level reaches a given level.

Thereafter, with the air stream supplied to the endoscope 123 for the predetermined time interval until the given pressure level appears, the leaked water detecting pump 97 is turned off. Subsequently, the leaked water detecting sensor 93 measures an internal pressure of the duct 54k, thereby checking whether or not the water leakage area is formed in the interior of the endoscope 123.

Figure 22:
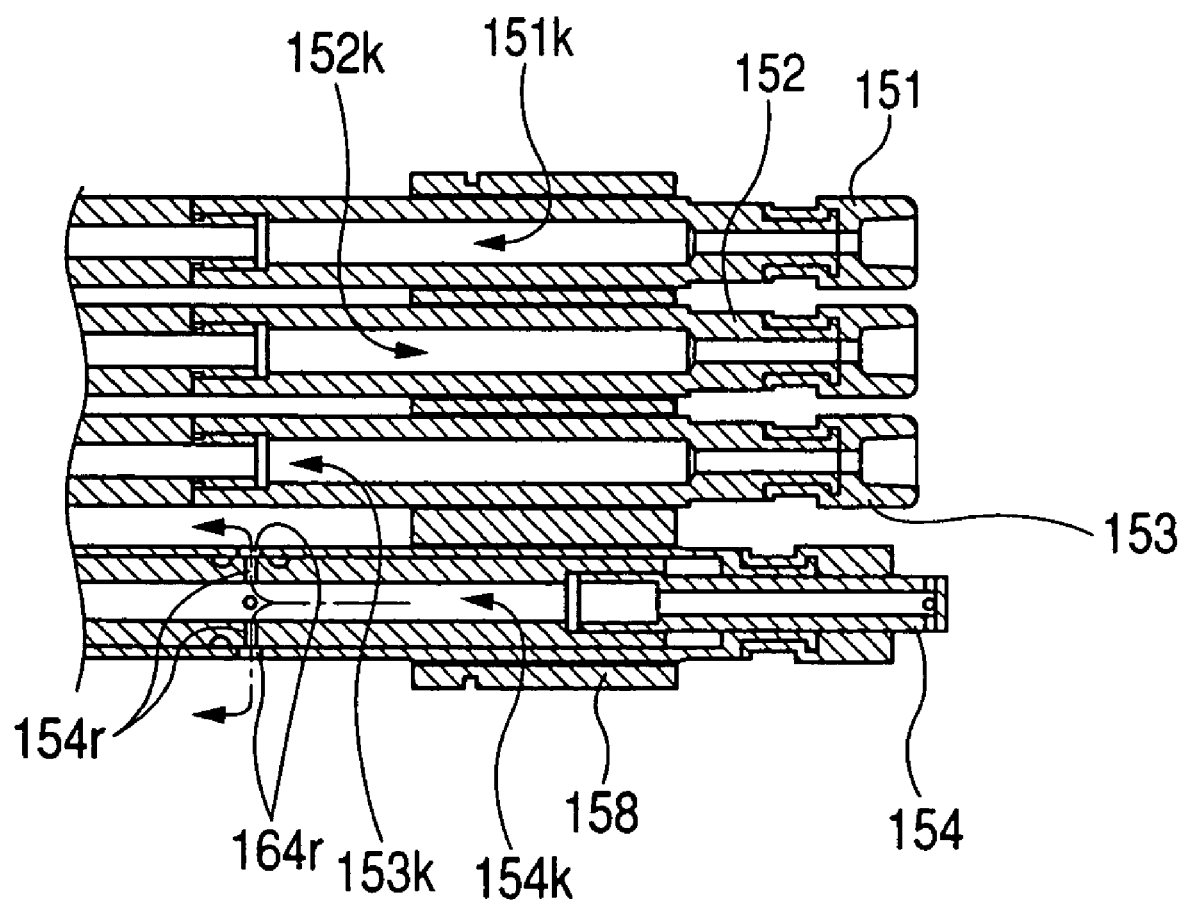
FIG. 22 is a partial cross sectional view of the first fluid supply unit remaining in a relief position.

Next, the controller 1 executes operation control such that only the water leakage detecting nozzle 154 moves backward with the movement of the shift member 191 until the communication apertures 154r, formed on the water leakage detecting nozzle 154, and the communication apertures 164r, formed on the pipe-like member 164, match each other as shown in FIG. 22. Even under such a condition, also, the duct 154k of the water leakage detecting nozzle 154 remains in communication with the inside of the endoscope 123.

Lastly, the controller 1 executes operation control so as to turn on the motor 181. At this moment, the rack gear 193, held in meshing engagement with the reduction gear train 182, is caused to rotate at a reduced speed in a reverse direction opposite to the direction in which the motor 181 is rotated before the shifting operation is initiated. This allows the shift member 191 to move at a low speed in a direction to be closer to the sidewall 105s in a direction perpendicular to the sidewall 105s.

As a result, the first fluid supply unit 150 is retracted from the duct coupling section 123 to the initial coupling position as shown in FIGS. 18 and 19. More particularly, only the distal end of the duct 154k of the water leakage detecting nozzle 154 is uncoupled from the water leakage detecting duct fitting 174. As a result, the spring 174d allows the valve body 174b to protrude, thereby causing the flange 174f to close the valve body 174b.

In addition, during the movement of the first fluid supply unit 150 is retracted from the duct coupling section 123 to the initial coupling position, the sleeve member 155 remains in abutting engagement with the distal end of the water leakage detecting duct fitting 174.

Thus, with the water leakage detecting duct fitting 174 and the inside of the sleeve member 155 remain closed in watertight relation, the distal end of the duct 154k of the water leakage detecting nozzle 154 is uncoupled from the water leakage detecting duct fitting 174, thereby closing the valve body 174b.

Therefore, even if the first fluid supply unit 150 is uncoupled from the duct coupling section 123 in liquid, no liquid droplet penetrates from the water leakage detecting duct fitting 174 into the inside of the endoscope 120.

More particularly, during the disinfecting step executed subsequent to the operation of checking water leakage, the forward water supply duct fitting 171, the water supply duct fitting 172 and the gas supply duct fitting 173 are disinfected. Therefore, even if the first fluid supply unit 150 is uncoupled from the duct coupling section 123, no liquid droplet penetrate from the water leakage detecting duct fitting 174 into the inside of the endoscope 123. Thus, the apical surface 123s and the forward water supply duct fitting 171, the water supply duct fitting 172 and the gas supply duct fitting 173 can be immersed in disinfecting liquid.

After the first fluid supply unit 150 has been uncoupled from the duct coupling section 123 to the initial coupling position, the forward water supply nozzle 151 of the first fluid supply unit 150 supplies disinfecting liquid or washing liquid to the forward water supply duct fitting 171 of the duct coupling section 123 and the water supply nozzle 152 supplies disinfecting liquid or washing liquid to the water supply duct fitting 172. Meanwhile, the gas supply nozzle 153 supplies disinfecting liquid or washing liquid to the gas supply duct fitting 173. In such a way, the known washing and disinfecting step is executed.

Also, the following steps are well known and, hence, description of the same is herein omitted. Further, the other operations are similar to those of the first embodiment set forth above and, hence, description of the same is herein omitted.

Thus, with the present embodiment, even if the respective duct fittings 171 to 174 are placed on the duct coupling section 123 of the endoscope 120 on the same plane in parallel to each other in one row, only one motor 181 allows the first fluid supply unit 150 to be controllably operated in an easy fashion to enable the respective nozzles 151 to 154 to be coupled to or uncoupled from the respective duct fittings 171 to 174, thereby enabling the endoscope to be washed and disinfected within a shortened period of time.

Further, during a phase in which the water leakage detecting nozzle 154 is automatically inserted to the water leakage detecting duct fitting 174, the water leakage detecting nozzle 154 is caused to inject air, thereby reshifting liquid from a space between the water leakage detecting nozzle 154 and the sleeve member 155 covering the outer periphery of the water leakage detecting nozzle 154. This also removes liquid adhered onto the neighborhood of the water leakage detecting duct fitting 174, disposed on the duct coupling section 123 of the endoscope 120 and placed in face-to-face relation to the water leakage detecting nozzle 154. This results in capability of preventing liquid from entering from the water leakage detecting duct fitting 174 into the inside of the endoscope 120 in a highly reliable manner during coupling and uncoupling operations.

Further, under a condition where the water leakage detecting duct fitting 174 and the sleeve member 155 remain tightly closed in watertight relation during a phase in which the water leakage detecting nozzle 154 is coupled to or uncoupled from the water leakage detecting duct fitting 174, the valve body 174b is closed or opened. Therefore, during the coupling and uncoupling operations, liquid can be reliably prevented from entering from the water leakage detecting duct fitting 174 into the inside of the endoscope 120. Also, the other effects are Identical to those of the first embodiment.

By the way, the endoscope washing and disinfecting apparatus according to the present embodiment is able to cope with washing and disinfecting, besides the endoscopes, other medical tools, such as therapeutic instruments with ducts or tubular through-ducts and over tubes.

Although the description above contains many specificities, these should not be construed as limiting the scope of the invention but as merely providing illustrations of some of the presently preferred embodiments of the present invention. Thus the scope of the present invention should be determined by the appended claims,

What is claimed is:

1. A method of supplying a gas through a nozzle to a fitting attached to an opening of a duct provided in an endoscope to sense a water leakage of the endoscope, comprising the steps of:
    starting the supply of the gas through the nozzle under a condition in which the nozzle is not coupled to the opening, the gas being supplied at a first pressure in order to remove and prevent liquid drops from forming inside the endoscope;
    moving the nozzle toward the opening after the start of the supply of the gas;
    inserting the nozzle into the opening until the nozzle is coupled to the opening;
    supplying the gas at a second pressure to sense a water leakage from inside of the endoscope after the nozzle is coupled to the opening and determining whether or not there is a water leakage based on the pressure inside of the endoscope; wherein
    the first pressure is greater than the second pressure.

2. The method of claim 1, wherein an amount of gas to be supplied through the nozzle is adjustable.

3. The method of claim 1, further comprising a step of returning the nozzle to an initial position after the determination of the water leakage is completed.

* * * * *

UNITED STATES PATENT AND TRADEMARK OFFICE
CERTIFICATE OF CORRECTION

PATENT NO.        : 7,875,126 B2
APPLICATION NO.   : 11/599812
DATED             : January 25, 2011
INVENTOR(S)       : Toshiaki Noguchi et al.

It is certified that error appears in the above-identified patent and that said Letters Patent is hereby corrected as shown below:

Column 26, line 52 (Claim 1, line 13) should read: coupled to the opening; and

Column 26, line 53 (Claim 1, line 14) should read: supplying the gas from the nozzle at a second pressure to sense a water Signed and Sealed this
Fifteenth Day of March, 2011

David J. Kappos
*Director of the United States Patent and Trademark Office*